United States Patent
Fateh

(10) Patent No.: US 10,441,214 B2
(45) Date of Patent: *Oct. 15, 2019

(54) MONITORING ADHERENCE TO A MEDICATION REGIMEN USING A SENSOR

(71) Applicant: Kali Care, Inc., Mountain View, CA (US)

(72) Inventor: Sina Fateh, Mountain View, CA (US)

(73) Assignee: KALI CARE, INC., Santa Clara, CA (US)

( * ) Notice: Subject to any disclaimer, the term of this patent is extended or adjusted under 35 U.S.C. 154(b) by 1244 days.

This patent is subject to a terminal disclaimer.

(21) Appl. No.: 14/608,704

(22) Filed: Jan. 29, 2015

(65) Prior Publication Data

US 2016/0220180 A1    Aug. 4, 2016

(51) Int. Cl.
*A61M 5/32* (2006.01)
*A61B 5/00* (2006.01)
(Continued)

(52) U.S. Cl.
CPC ........... *A61B 5/4833* (2013.01); *A61J 7/0427* (2015.05); *G06F 19/3462* (2013.01);
(Continued)

(58) Field of Classification Search
CPC .............. A61B 5/4833; A61B 5/02438; A61B 5/14532; A61B 5/14542; A61B 5/4839;
(Continued)

(56) References Cited

U.S. PATENT DOCUMENTS

| 5,152,424 A | 10/1992 | Weinreb et al. |
| 7,949,426 B2 | 5/2011 | Handfield et al. |

(Continued)

FOREIGN PATENT DOCUMENTS

| CN | 1759398 A | 4/2006 |
| CN | 201173771 Y | 12/2008 |

(Continued)

OTHER PUBLICATIONS

Extended European Search Report dated Dec. 15, 2017 for European Patent Application No. 16744225.0, 9 pages.

(Continued)

*Primary Examiner* — Andrew J Mensh
(74) *Attorney, Agent, or Firm* — Perkins Coie LLP

(57) ABSTRACT

A method and apparatus for monitoring and/or managing adherence to a medication regimen that involves use of a sensor. Dispensing medicine from a container commonly involves pressure being applied to the container, which results in expansion of the container. In some embodiments, pressure is applied by a user through an aperture of the apparatus. In some embodiments, a processor monitors pressure sensor data from a pressure sensor that is physically coupled to the container and arranged such that activation of the pressure sensor indicates the container has expanded in response to the user applying pressure. A processor analyzes the pressure sensor data to determine whether medicine has been dispensed from the container. A computer system can compare the dispensed medication to a planned medication regimen to determine a state of compliance with the medication regimen.

19 Claims, 20 Drawing Sheets

(51) Int. Cl.
*G06F 19/00* (2018.01)
*A61J 7/04* (2006.01)
*A61B 5/145* (2006.01)
*A61B 5/024* (2006.01)

(52) U.S. Cl.
CPC ....... *A61B 5/02438* (2013.01); *A61B 5/14532* (2013.01); *A61B 5/14542* (2013.01); *A61B 5/4839* (2013.01); *A61B 5/6898* (2013.01)

(58) Field of Classification Search
CPC ... A61B 5/6898; G06F 19/00; G06F 19/3462; A61J 7/0427
USPC ........................................................ 604/404
See application file for complete search history.

(56) References Cited

U.S. PATENT DOCUMENTS

| | | | |
|---|---|---|---|
| 8,998,861 B2 | 4/2015 | Fateh | |
| 9,728,068 B2 | 8/2017 | Engelhard et al. | |
| 2004/0039355 A1* | 2/2004 | Gonzalez | A61F 9/0008 604/298 |
| 2004/0188290 A1 | 9/2004 | Sterns | |
| 2004/0204674 A1* | 10/2004 | Anderson | A61M 5/1723 604/66 |
| 2006/0071825 A1 | 4/2006 | Demos | |
| 2007/0024465 A1 | 2/2007 | Howell et al. | |
| 2009/0045078 A1 | 2/2009 | Gelardi et al. | |
| 2009/0240215 A1 | 9/2009 | Humayun et al. | |
| 2009/0259204 A1 | 10/2009 | Galdeti et al. | |
| 2009/0306633 A1* | 12/2009 | Trovato | A61B 1/041 604/891.1 |
| 2010/0286634 A1* | 11/2010 | Marx | A61F 9/0026 604/302 |
| 2011/0025830 A1 | 2/2011 | Mcnamer et al. | |
| 2011/0264028 A1 | 10/2011 | Ramdas et al. | |
| 2012/0143152 A1* | 6/2012 | Hunter | A61B 5/0059 604/298 |
| 2012/0176506 A1 | 7/2012 | Tajiri | |
| 2012/0222979 A1 | 9/2012 | Baym et al. | |
| 2014/0062918 A1 | 3/2014 | Chen et al. | |
| 2014/0081100 A1 | 3/2014 | Muhsin et al. | |
| 2014/0228783 A1 | 8/2014 | Kraft | |
| 2014/0257206 A1 | 9/2014 | Fateh | |
| 2014/0262918 A1 | 9/2014 | Chu | |
| 2014/0276476 A1 | 9/2014 | Fateh | |
| 2015/0173945 A1 | 6/2015 | Fateh et al. | |
| 2016/0155267 A1 | 6/2016 | Bean et al. | |
| 2016/0239635 A1 | 8/2016 | Fateh | |
| 2017/0173262 A1 | 6/2017 | Veltz | |
| 2017/0340846 A1 | 11/2017 | Gramann et al. | |
| 2017/0357775 A1 | 12/2017 | Ekin | |
| 2018/0042417 A1 | 2/2018 | Brown et al. | |

FOREIGN PATENT DOCUMENTS

| | | |
|---|---|---|
| EP | 1656923 A1 | 5/2006 |
| GB | 2418049 A | 3/2006 |
| JP | H09226785 A | 9/1997 |
| JP | 2003117988 A | 4/2003 |
| JP | 2007525276 A | 9/2007 |
| JP | 2008532568 A | 8/2008 |
| JP | 2006511263 A | 4/2009 |
| JP | 5028637 B2 | 7/2012 |
| JP | 2013529117 A | 7/2013 |
| JP | 2014513612 A | 6/2014 |
| JP | 2014528793 A | 10/2014 |
| JP | 2016537810 A | 12/2016 |
| WO | 0124690 A2 | 4/2001 |
| WO | 2004028420 A1 | 4/2004 |
| WO | 2011113028 A2 | 9/2011 |
| WO | 2013043607 A1 | 3/2013 |
| WO | 2014004437 A1 | 1/2014 |
| WO | 2015002492 A1 | 1/2015 |

OTHER PUBLICATIONS

Final Office Action dated Jun. 16, 2016 for U.S. Appl. No. 13/844,233 of Fateh, S, filed Mar. 15, 2013.
Final Office Action dated Jun. 9, 2017 for U.S. Appl. No. 13/844,233 of Fateh, S, filed Mar. 15, 2013.
Non-Final Office Action dated Mar. 30, 2018 for U.S. Appl. No. 14/621,293 of S. Fateh filed Feb. 12, 2015.
Notice of Allowance dated May 16, 2018 of U.S. Appl. No. 13/844,233 of Fateh, S., filed Mar. 15, 2013.
Notification of Registration and Granting a Patent Right dated Mar. 28, 2018, for Chinese Patent Application No. 201380067442.1, 10 pages.
Restriction Requirement dated Jan. 5, 2018 for U.S. Appl. No. 14/621,293 of Fateh, S. filed Feb. 12, 2015.
Second Office Action dated Feb. 21, 2017, for Chinese Patent Application No. 201380067442.1, 18 pages.
Supplementary European Search Report dated Oct. 9, 2017 for European Patent Application No. 16749887.2, 8 pages.
Third Office Action dated Sep. 19, 2017, for Chinese Patent Application No. 201380067442.1, 10 pages.
Extended European Search Report dated May 27, 2016 for EP Patent Application No. 13848685.7, 9 pages.
First Office Action dated Mar. 25, 2016, for Chinese Patent Application No. 201380067442.1, 21 pages.
International Search Report and Written Opinion dated Jun. 30, 2016, for International Application No. PCT/US2016/017563 filed Feb. 11, 2016, 7 pages.
International Search Report and Written Opinion dated May 19, 2016, for International Application No. PCT/US16/15784 filed on Jan. 29, 2016, 7 pages.
International Search Report and Written Opinion of International Application No. PCT/US2013/066450, dated Feb. 14, 2014.
Non-Final Office Action dated Aug. 29, 2014 for U.S. Appl. No. 14/281,001 of Fateh, S. et al. filed May 19, 2014.
Notice of Allowance dated Jan. 13, 2015 for U.S. Appl. No. 14/281,001 of Fateh, S., et al. filed May 19, 2014.
Restriction Requirement dated Aug. 7, 2015 in Co-Pending U.S. Appl. No. 13/844,233 of Fateh, S., filed Mar. 15, 2013.
U.S. Appl. No. 14/621,293 of Fateh, S., filed Feb. 12, 2015.
Non-Final Office Action dated Oct. 30, 2015, for U.S. Appl. No. 13/844,233 of Fateh, S. filed Mar. 15, 2013.
Final Office Action dated Jul. 26, 2018 for U.S. Appl. No. 14/621,293 of S. Fateh filed Feb. 12, 2015.
Non-Final Office Action dated Jul. 26, 2018 for U.S. Appl. No. 14/639,989 of Fateh, S., filed Mar. 5, 2015.
Notice of Allowance dated Aug. 1, 2018 for U.S. Appl. No. 13/844,233 of Fateh, S., filed Mar. 15, 2013.

* cited by examiner

MONITORING ADHERENCE TO A MEDICATION REGIMEN USING A SENSOR

TECHNICAL FIELD

Various embodiments of the present invention generally relate to medication management. More specifically, some embodiments of the present invention relate to systems and methods for monitoring adherence to a medication regimen using a sensor.

BACKGROUND

Approximately thirty percent of medication prescriptions are never filled. In addition, approximately fifty percent of medications for chronic disease are not taken as prescribed. This lack of adherence has dramatic effects on health. Non-adherence has been estimated to cost the U.S. health care system $200 billion annually. As one example, in ophthalmology, compliance to the medication plan, also referred to as the medication regimen, is vital for preventing visual loss and blindness that may result from chronic conditions such as glaucoma. Almost seventy-five percent of patients admit to some form of noncompliant behavior, over thirty percent do not fill their prescriptions, and nearly fifty percent discontinue their prescriptions within six months.

While forgetfulness is one barrier to medication adherence, it is not the only barrier. In addition, taking the medication at the wrong time, stopping too early, or taking the wrong dose also represent other serious barriers. Unfortunately, there are no effective systems for managing adherence to a medication regimen which can be vital for maintaining or improving health.

BRIEF DESCRIPTION OF THE DRAWINGS

Embodiments of the disclosed technology will be described and explained through the use of the accompanying drawings in which.

Figure 1:
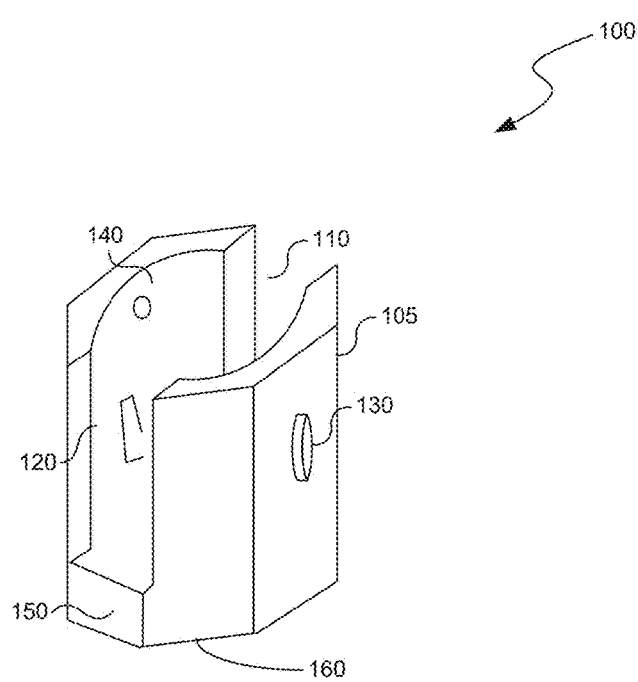
FIG. 1 illustrates an example of a medication device, consistent with various embodiments.

The drawings have not necessarily been drawn to scale. For example, the dimensions of some of the elements in the figures, such as the elements of the medication device embodiments of FIGS. 1-4 and 12-15 or the medicine dispensing system of FIG. 6, may be expanded or reduced to help improve the understanding of the embodiments of the present invention. Similarly, some components and/or operations may be separated into different blocks or combined into a single block for the purposes of discussion of some of the embodiments of the present invention. Moreover, while the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Various embodiments of the disclosed technology generally relate to medication management. More specifically, some embodiments of the present invention relate to systems and methods for monitoring and/or managing adherence to and/or compliance with a medication regimen via use of a sensor, such as a pressure sensor of a medication device or a motion sensor of a mobile device. A medication regimen is a plan about medicine to make a person become or stay healthy. A medication regimen, for example: can identify one or more medications that the person is to take or have administered; can identify the frequency and/or time that a dose or doses of a medication are to be taken or administered; can identify the amount or quantity of a dose of the medication to be taken or administered; and/or can identify the duration of time, such as the length of time or the start and end times, that a medication is to be taken or administered.

There are many reasons why a person may not adhere to and/or comply with a medication regimen: forgetting to take the medication; misunderstanding the regimen; making an error about the amount or quantity of a dose of the medicine or the time at which to take the dose; forgetting to refill a prescription; being unable to afford the medication; etc. This lack of adherence may result in a severe impact to the person's health. Further, there may be a number of people who have a vested interest in whether a person is adhering to a medication regimen, such as the person him or herself, a relative of the person, the person's doctor or other medical staff, etc. For example, a child of an elderly parent may want to know when his parent is not adhering to a medication regimen, so that he can take actions to identify the reason(s) for the non-adherence and take action to address those reasons.

The disclosed technology enables a person's adherence and/or compliance to a medication regimen to be monitored and/or managed. Dispensing medicine from a container commonly involves motion of the container, which can be a distinctive motion. For example, when dispensing pills from a bottle, a user may lift the bottle and tilt and shake it so that one or more pills fall through a hole at one end of the bottle. Motion sensor data is data generated by a motion sensor. Motion sensor data generated by a motion sensor that moves in unison with a container can indicate the tilting and shaking that occurs as medicine is being dispensed. The motion sensor data can further indicate vibrations, such as from the medicine shifting in the container while being dispensed. In another example, a user tilts and positions an eye dropper above an eye, and squeezes the eye dropper to dispense a liquid eye medicine into the eye. In yet another example, a user shakes a pressurized inhaler to mix the medicine, positions the inhaler at his mouth, and triggers a mechanism that causes the medicine to be ejected from the inhaler via a release of the pressurized gas. Each of these examples of medicine being dispensed from a container can involve a distinct motion of the container.

Motion sensor data can be analyzed to determine the physical movement or motion of the motion sensor that generates the motion sensor data. For example, a motion sensor can generate data representing an acceleration vector for the motion sensor, which can indicate an acceleration of the motion sensor along that vector. In some embodiments, a motion sensor can move in unison with the container. An analysis of the motion sensor data to determine the associated motion sensor motion can, correspondingly, also determine the associated container motion. The motion can be analyzed to determine if it matches a distinctive motion of a medication being dispensed, and, accordingly, to determine whether the medication was dispensed.

In some embodiments, the motion sensor data and/or the associated indicated motion can be further analyzed to determine the amount or quantity of the medication in the dose of the medicine. For example, an inhaler can exhibit a distinctive motion when a dose of medicine is ejected from the inhaler via a release of pressurized gas. If a user releases multiple doses of medicine from the inhaler, both the inhaler and the motion sensor with which it moves in unison can exhibit the distinctive motion each time one of the doses is released.

In some embodiments, the motion sensor moves in unison with the container by being physically coupled with the container. In one example, the container, which contains medicine, is inserted in and held by a medication device. The medication device is also connected to a mobile device, such as a smart phone. The container, the medication device, and the smart phone are all physically coupled, which causes all three objects to move in unison. The smart phone includes a motion sensor which generates motion sensor data that indicates the motion of the motion sensor. Because the motion sensor is moving in unison with all of the container, the medication device, and the mobile device, the motion sensor data also indicates the motion of these three objects.

In some embodiments, an application running on the smart phone can analyze the motion sensor data to determine the physical movement or motion of a container to which the smart phone is physically coupled. If the motion matches a distinctive motion of a dose of a medication being dispensed, the application can determine that a dose of the medication was dispensed. The application can further analyze the motion sensor data to determine the amount or quantity of the medication that was dispensed in the dose.

Sensor data can also be gathered by a pressure sensor and analyzed by a processor to determine whether medication has been dispersed. In some embodiments, the medication device comprises a jacket, which is configured to hold a container of medicine and includes an aperture. The aperture allows a user to apply pressure to the container to dispense medicine. In some embodiments, a pressure sensor is coupled to the jacket and configured to sense lateral expansion of the container in response to the user applying pressure to the container through the aperture. The pressure sensor may, for example, be positioned inside an interior cavity of the jacket. In some embodiments, the medication device further comprises a wireless communication module configured to exchange data recorded by the pressure sensor with a communications device. The data can be analyzed to determine whether the proper amount of medicine was distributed at the proper time in accordance with a medication regimen.

In some embodiments, the medication device contains a sensor to sense the medication being dispensed, and the medication device can communicate with the smart phone, such as via Bluetooth or a direct connection using a connector such as Lightning or microUSB. In one example, as the motion sensor moves, it generates motion sensor data that the application analyzes. When the application determines that the motion indicates that a medication may be about to be dispensed, the application sends a signal to the medication device to activate the sensor of the medication device.

The sensor is, in this example, an optical sensor that is used in combination with a laser to determine when medicine is dispensed as indicated by the laser beam fluctuating and/or being interrupted. The laser and the associated sensor are positioned such that any medication leaving the container disrupts the laser beam. As the medication is dispensed, the application detects breaks or other disruptions of the laser beam based on the sensor data. The application further determines, based on the fluctuations in the sensor data, dose information, such as how many pills were dispensed in the current dose.

The current dose can be one of a number of doses of a medication regimen. In some embodiments, the smart phone determines the time and/or date that the dose was dispensed. The smart phone sends the dose information of the current dose, which can include the time/date that the dose was dispensed and/or administered, to a computer system. The smart phone can send the dose information to the computer system, for example, via a wireless network. The computer system can have access to a database that contains the medication regimen for the user. The computer system can compare the dose information to expected dose information as indicated by the medication regimen and determine whether the user is adhering to the medication regimen.

When the computer system determines that the user is not adhering to the medication regimen, the computer system can take an action based on this determination. For example, the computer system can send a message to any or all of a set of people who are listed in the database, such as the user, the user's relative, the doctor or other medical staff, etc. The message can notify the recipients of the non-compliance, and/or can send other compliance-related information.

In the following description, for the purposes of explanation, numerous specific details are set forth in order to provide a thorough understanding of embodiments of the present invention. It will be apparent, however, to one skilled in the art that embodiments of the present invention may be practiced without some of these specific details. While, for convenience, embodiments of the present invention are described with reference to monitoring the dispensing of medicine, embodiments of the present invention are equally applicable to monitoring the dispensing of various other types of material or liquid outside of the medical industry.

Further, physical coupling is not limited to the description of the above example. Two objects can be physically coupled in any of a variety of ways. For example, a first object can be physically coupled with a second object by being integrated with or connected to the second object, by being integrated with or connected to a third object that is connected to the second object, etc. When a first object is integrated with or connected to a second object, both objects resultantly move in unison.

Additionally, the motion sensor is not limited to being physically coupled to the container per the above example. In various embodiments, the motion sensor is physically coupled with the container: by being integrated with or connected to the container; by being integrated with or connected to a medication device that is connected to or holding the container; by being integrated with or connected to a mobile device that is connected to the container; by being integrated with or connected to a mobile device that is connected to a medication device that is connected to or holding the container; etc. As these examples illustrate, the motion sensor can be integrated with or connected to the container, the medication device, or the mobile device, as well as other objects, when moving in unison with the container.

Moreover, the techniques introduced here can be embodied as special-purpose hardware (e.g., circuitry), as programmable circuitry appropriately programmed with software and/or firmware, or as a combination of special-purpose and programmable circuitry. For example, in some embodiments, the medication device discussed above includes special purpose hardware for processing and analyzing the sensor data that is discussed above. Hence, embodiments may include a machine-readable medium having stored thereon instructions that may be used to program a computer (or other electronic devices) to perform a process. The machine-readable medium may include, but is not limited to, floppy diskettes, optical disks, compact disc read-only memories (CO-ROMs), magneto-optical disks, ROMs, random access memories (RAMs), erasable programmable read-only memories (EPROMs), electrically erasable programmable read-only memories (EEPROMs), magnetic or optical cards, flash memory, or other types of machine-readable mediums suitable for storing electronic instructions. Additional variations on the above examples will be discussed below.

Terminology

Brief definitions of terms, abbreviations, and phrases used throughout this application are given below.

The phrases "in some embodiments," "according to some embodiments," "in the embodiments shown," "in other embodiments," and the like generally mean the particular feature, structure, or characteristic following the phrase is included in at least one implementation of the present invention, and may be included in more than one implementation. In addition, such phrases do not necessarily refer to the same embodiments or different embodiments.

If the specification states a component or feature "may", "can", "could", or "might" be included or have a characteristic, that particular component or feature is not required to be included or have the characteristic.

The term "module" refers broadly to a software, hardware, or firmware (or any combination thereof) component. Modules are typically functional components that can generate useful data or other output using specified input(s). A module may or may not be self-contained. An application program (also called an "application") may include one or more modules, or a module can include one or more application programs.

The term "cause" and variations thereof refer to either direct causation or indirect causation. For example, a computer system can "cause" an action by sending a message to a second computer system that commands, requests, or prompts the second computer system to perform the action. Any number of intermediary devices may examine and/or relay the message during this process. In this regard, a device can "cause" an action even though it may not be known to the device whether the action will ultimately be executed.

General Description

FIG. 1 illustrates an example of a medication device 100, consistent with various embodiments. As illustrated in FIG. 1, medication device 100 provides a jacket or expansion pack 105 to enclose a container containing material or liquid within opening 110, such as a bottle containing eye drops or pills, or an inhaler containing a gas, liquid, or powder. Jacket 105 can include a wing pressure mechanism 120, a tactile sensor 130, a material/drop sensor 140, and an electronic module compartment 150. Wing pressure mechanism 120 provides a mechanism for securing a container within opening 110 of jacket 105. In other embodiments, other mechanisms may be used to secure the container. For example, inserts of different sizes may be sized to fit securely within opening 110 of jacket 105, and at the same time, provide a smaller opening for securing the container. In other cases, different materials may be used to line jacket 105 that are flexible enough to allow for insertion of containers of varying sizes and shapes. Still yet, various mechanical levers and gripping members may be used to secure the container within jacket 105.

Tactile sensor 130 can be used to provide a touch input interface (e.g., to detect the finger of a user). The user's touch can then activate/deactivate (i.e., turn on-off) the device. In some embodiments, tactile sensor 130 can also detect and record other types of data such as pulse, heart rate, oxygen saturation, glucose concentration within the bloodstream, etc. In some embodiments, the medication device 100 acquires medical information (e.g., heart rate, glucose concentration) from another distinct device worn by the user. The medication device 100 can modify one or more doses of medicine to be dispensed based on the pulse, heart rate, etc., measured by the medication device 100 or another device worn by the user. For example, the medication device 100 can personalize the dose (i.e., increase, reduce, refuse to deliver) if the user's blood pressure is determined to be too high. The information gathered by the medication device 100 or other wearable device can be analyzed locally (e.g., electronic module compartment 150) or remotely (e.g., transmitted to a cloud storage database). In some embodiments, the medication device 100 includes a sensor to measure temperature, humidity, pressure (e.g., barometer), etc. The sensors can be used, for example, to test for environmental stimuli that cause or aggravate ocular conditions (e.g., dry eye, glaucoma).

Material/drop detector sensor 140 can detect when matter, such as a pill or a drop of liquid, leaves a container. Material/drop sensor 140 could be an optical (e.g., light emitting diode (LED)/phototransistor) sensor capable of detecting if some matter has been released from the container. In these cases, when the matter is released from the bottle, the drop will block or refract a beam and cause the output of the optical sensor to fluctuate. Material/drop sensor 140 can be placed at the top of the expansion pack and could be activated only when the container is in a specific position, as detected by a motion detector, to conserve power. While a specific jacket configuration and sensor type are discussed here, it is understood that a wide variety of jacket configurations and sensor types can be used to hold various types of containers, and to detect when matter is dispensed or released from the container.

In some embodiments, electronic module compartment 150 houses motion sensor 160, and can house additional modules and/or components (e.g., processors, communication devices, integrated electronics, memory storage devices, batteries, sensors, etc.) of the medication device. For example, in some embodiments, electronic module compartment 150 can include a gesture recognition module. The gesture recognition module can be used for detecting and providing the hand and bottle motion and position. In order to avoid false and unwanted motion measurement, in some embodiments, the gesture recognition module may be activated only when the tactile sensors detect a touch by a user's finger.

Figure 8A:
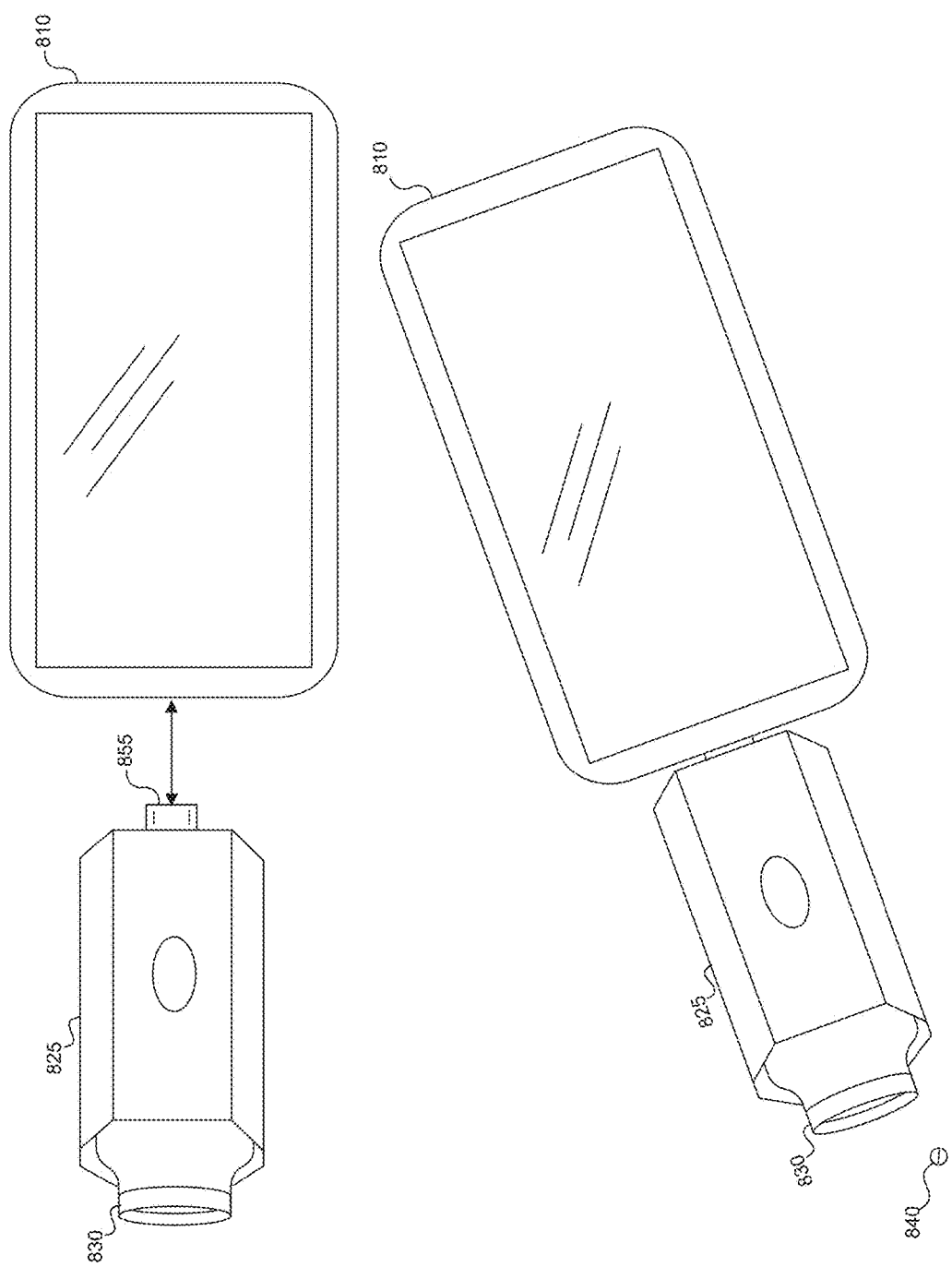
FIGS. 8A and 8B are, respectively, views of a first and a second medication device that attach to a smart phone via, respectively, a first and a second mechanism, consistent with various embodiments.
Figure 8B:
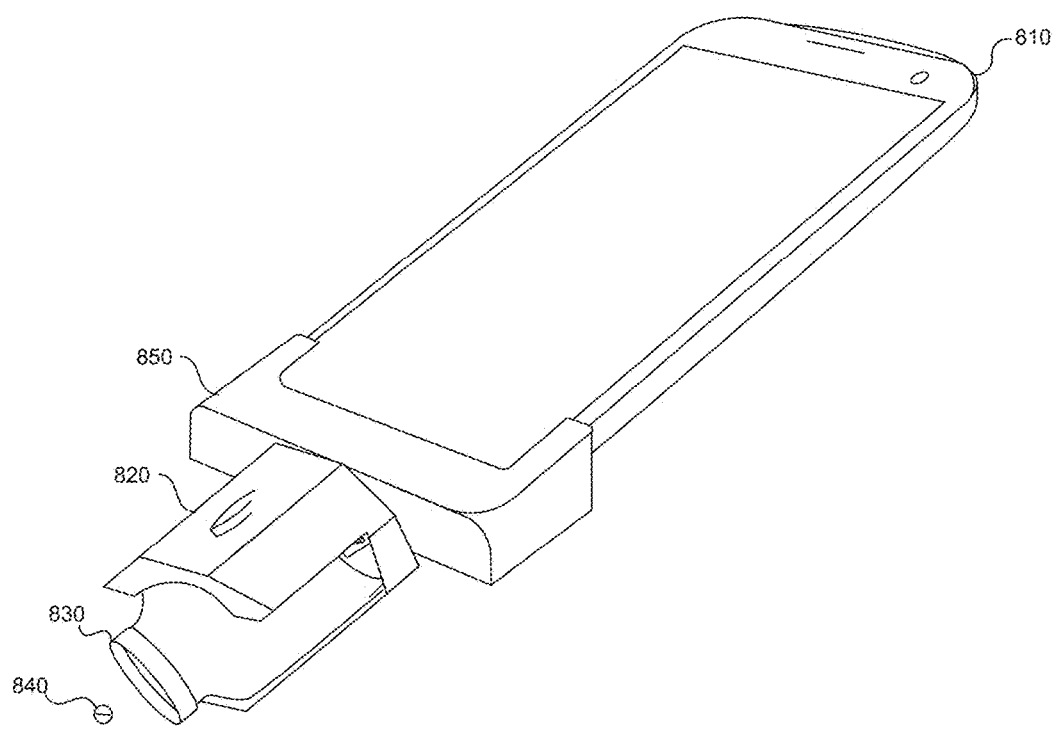

In some embodiments, motion sensor 160 generates signals that indicate the physical movement or motion of the motion sensor. Because motion sensor 160 is attached to or embedded in medication device 100 and, resultantly, moves in unison with medication device 100, the generated signals also indicate the motion of medication device 100, and of any container that is held by or otherwise physically connected to medication device 100. In some embodiments, the motion of medication device 100 can be indicated by a motion sensor of a mobile device to which medication device 100 is physically connected, as will be discussed in more detail below. Motion sensor 160, or a motion sensor of a mobile device to which medication device 100 is physically connected, can be used to indicate the position and motion of a container that is physically connected to medication device 100. FIGS. 8A and 8B illustrate, respectively, medication devices 825 and 820, medication devices that are similar to medication device 100, physically connected to smart phone 810, a mobile device, via different mechanisms.

As another example, a wireless communication module can be used to send and receive data to and from a computer and portable communication devices. An embedded controller module can include signal preprocessing electronics. Still yet, the module may include Bluetooth, cellular including 3G or 4G, Bluetooth Low Energy (BLE), near field communication (NFC), a wireless local area network (WLAN) transmitter (e.g., a WiFi/IEEE 802.11 compliant transmitter), or other wireless technology to send and load data to a mobile device or computer. Examples of mobile devices include smart phones, tablets, portable media devices, wearable devices, laptops, and other portable computers.

Figure 2:
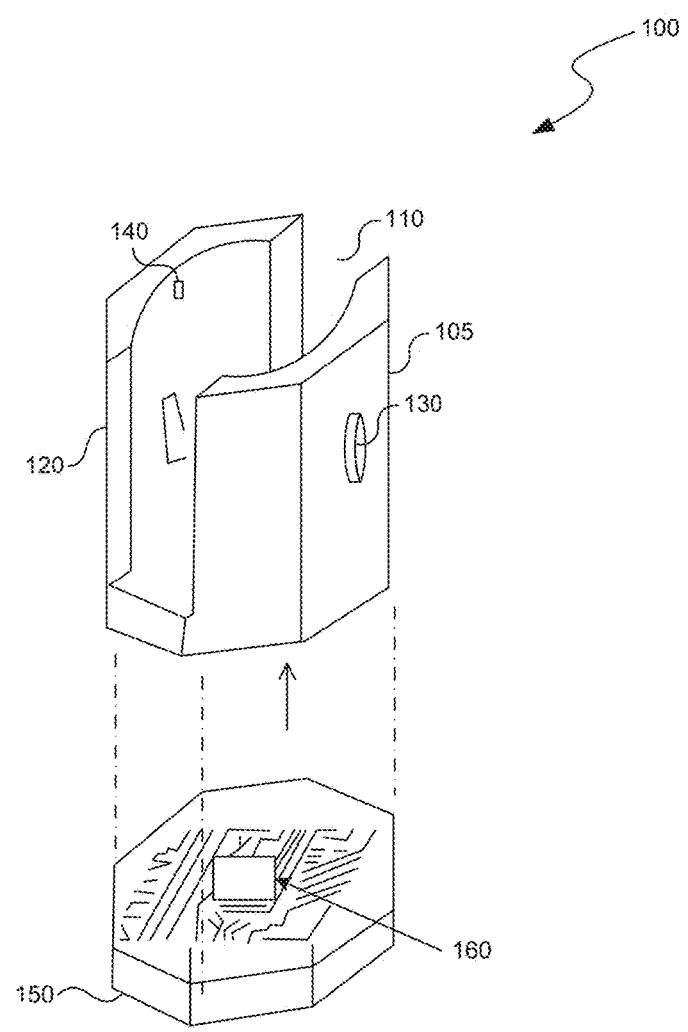
FIG. 2 is an expanded view of a medication device, consistent with various embodiments.

In some embodiments, jacket 105 may have integrated electronics and components embedded throughout. As illustrated in FIG. 2, electronic module compartment 150 can be removable from jacket 105. As a result, some embodiments provide for a plurality of jackets, each having openings of different sizes and lengths to hold different sized or shaped medicine containers. The jackets can be removed and interchanged with the electronic module compartment. The jackets can include mechanical, electrical, or electromechanical sensors for detecting that a bottle or other container is present within the jacket. For example, in some embodiments, optical components or switches may be used to detect that a bottle is present within the jacket.

Figure 3:
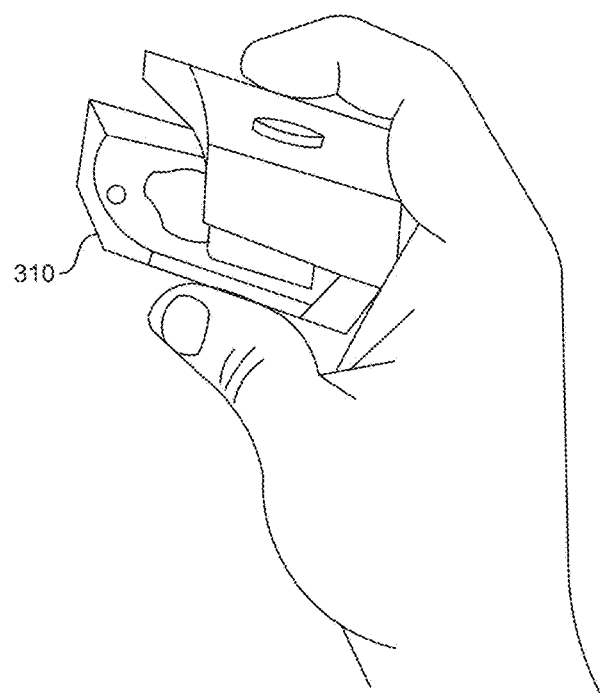
FIG. 3 is a side view of a user tilting a medication device, consistent with various embodiments.
Figure 4:
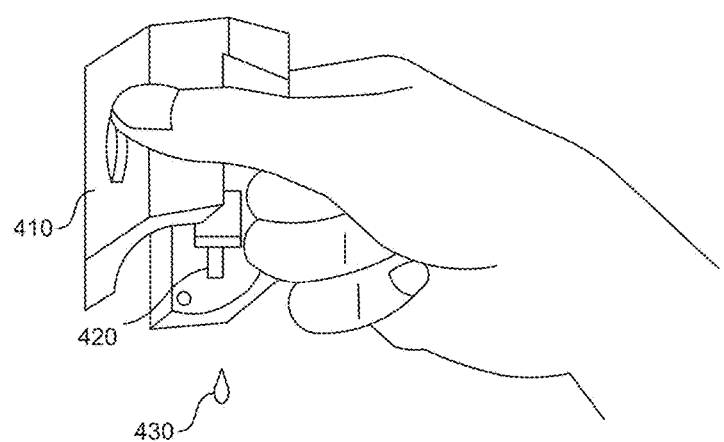
FIG. 4 is a view of a user using a medication device to distribute eye drops, consistent with various embodiments.
Figure 5:
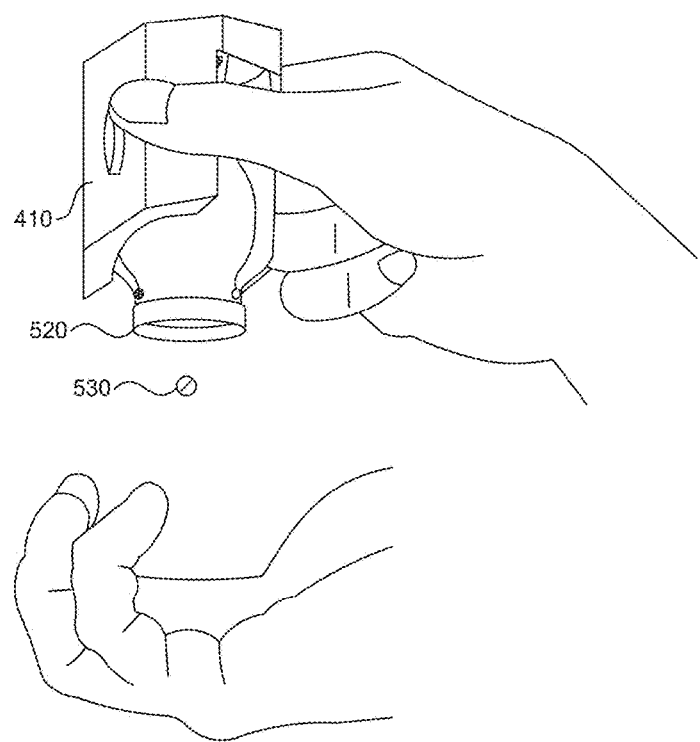
FIG. 5 is a view of a user using a medication device to distribute pills, consistent with various embodiments.

FIG. 3 is a side view of a user tilting a portable medication device 310, consistent with various embodiments. Once a container is placed within the device and a user begins to interact with portable medication device 310, various subsystems can be activated for tracking the user's activity. For example, when the user interacts (e.g., touches, moves, etc.) with the device, various sensors (e.g., drop sensors, motion sensors, etc.) can be activated. Then as the user tilts portable medication device 410 upside down, as illustrated in FIG. 4, the sensors can determine if matter, such as eye drop 430, was released from container 420. As another example, as the user tilts portable medication device 410 upside down, as illustrated in FIG. 5, the sensors can determine if matter, such as pill 530, was released from container 520.

Figure 6A:
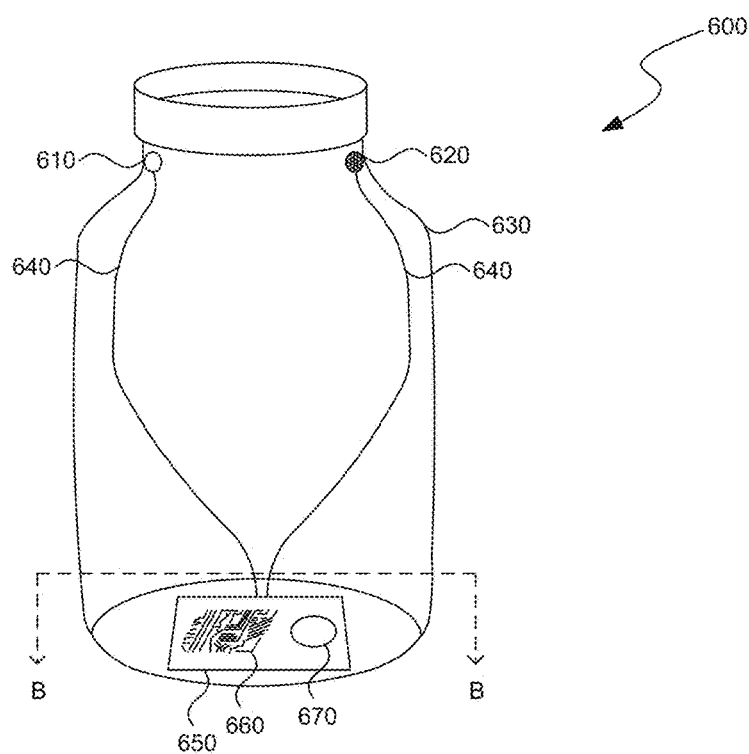
FIGS. 6A and 6B are, respectively, a view of a medicine dispensing system, and a view of the electronics at the bottom of the medicine dispensing system, consistent with various embodiments.
Figure 6B:
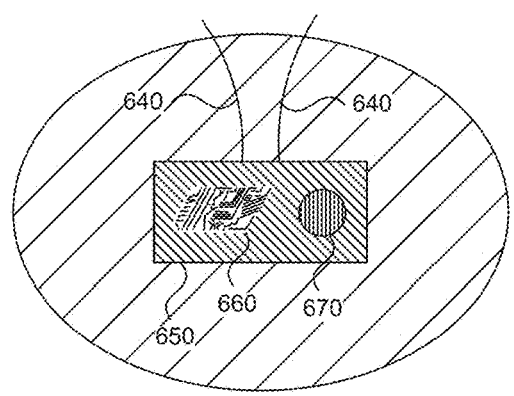

FIGS. 6A and 6B are, respectively, a view of a medicine dispensing system, and a view of the electronics at the bottom of the medicine dispensing system, consistent with various embodiments. Medicine dispensing system 600 includes LED 610, optical sensor 620, container 630, printed circuit board (PCB) 650, wires 640 which run in or on the sides of container 630 to connect LED 610 and optical sensor 620 to PCB 650, motion sensor 660 which is attached to or mounted on PCB 650, and battery 670 which is attached to or mounted on PCB 650. Container 630 can be used to store materials, such as medicines. As illustrated in FIG. 6, container 630 is for storing pills. In some embodiments, the container is designed to store other matter, such as liquids, powders, gels, gases, etc. For example, the container can be an inhaler, and the matter can be a gas, liquid, or powder, or the container can be a tube and the matter can be a gel such as an anti-fungal cream.

In the embodiment of FIG. 6, motion sensor 660 generates motion sensor data that indicates the physical movement or motion of medicine dispensing system 600. To conserve battery life, the electronics of medicine dispensing system 600 can be put in a low power state where a reduced set of electronics, which can include the motion sensor, is enabled. The electronics of medicine dispensing system 600 can include processors, communication devices, integrated electronics, memory storage devices, sensors, batteries, etc., some of which can be located on PCB 650, such as motion sensor 660 and battery 670.

Figure 7:
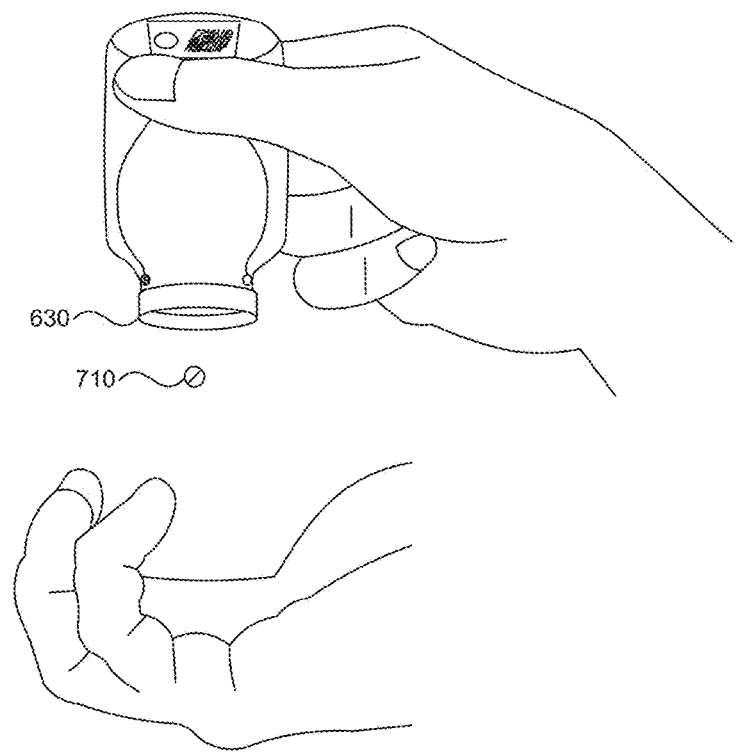
FIG. 7 is a view of a user using a medicine container to dispense a pill, consistent with various embodiments.

When medicine dispensing system 600 begins to move, such as when a user grabs the container to dispense the medicine, motion sensor 660 can send a signal that causes the electronics of medicine dispensing system 600 to wake up and become active. LED 610 turns on and begins emitting light, which is detected by optical sensor 620. When container 630 is tilted such that a pill is dispensed from the container, as is illustrated in FIG. 7, pill 710 disturbs the light passing from LED 610 to optical sensor 620, causing the output of optical sensor 620 to fluctuate. The optical sensor data can be sent to a processor, such as a processor of the electronics of medicine dispensing system 600, a processor of a mobile device, or a processor of a computer system, and the processor can analyze the optical sensor data.

For example, the optical sensor data can pass through wires 640 and PCB 650 to a processor mounted on the PCB where the processor analyzes the optical sensor data. In another example, the optical sensor data can pass through wires 640 and PCB 650 to a communication device mounted on the PCB, which sends the data wirelessly to a mobile device, where the processor of the mobile device analyzes the optical sensor data. In yet another example, the optical sensor data can pass through wires 640 and PCB 650 to a communication device mounted on the PCB, which sends the data wirelessly to a mobile device, which sends the data via a network to a computer system, where the processor of the computer system can analyze the optical sensor data. In one more example, the optical sensor data can pass through wires 640 and PCB 650 to a communication device mounted on the PCB, which sends the data wirelessly to a Wi-Fi router, which sends the data via a network to a computer system, where the processor of the computer system analyzes the optical sensor data.

A processor that analyzes the optical sensor data can determine, based on the analysis, whether any matter was released from the container, such as a pill. Further, the processor can analyze the data to determine how many pills were released from the container, and can accordingly determine the amount or quantity of the dose of the medicine that was dispensed.

In various embodiments, data from any of a variety of types of sensors can be used by the processor to determine whether any medicine was released from the container, and to determine the amount or quantity of the dose of the medicine that was released. The types of sensors can include a pressure sensor, an optical sensor, a sound sensor, an electrical current sensor, a fluid sensor, a fluid velocity sensor, a force sensor, a chemical sensor, a magnetic field sensor, an electrical field sensor, a drop sensor, a heat sensor, a tactile sensor, etc.

For example, data from a pressure sensor or a sound sensor can be used by a processor to determine whether the medicine of an inhaler was released, and how much medicine was released. The determination can be made based on the detected pressure of the gas inside the inhaler, or the detected sound of pressurized gas being released from the inhaler. As another example, data from a pressure sensor that is located on the bottom of the container, and that receives pressure in proportion to the weight of the container when the container is placed on a surface, can be used by a processor to determine the weight of the medicine that was dispensed from the container. As yet another example, data from a sound sensor can be used by a processor to determine whether a pill was released from a bottle based on the sounds a pill makes when released from a bottle.

In some embodiments, the processor can determine if any matter was released from the container based on data from motion sensor 660. When a user dispenses medication from a container, the container may exhibit a distinctive motion. For example, if the motion of container 630 being moved from one location to another is compared to the motion of container 630 being tilted and shaken to cause a pill to be released from the container, those motions are quite different. The motion of the container being tilted and shaken can be quite distinctive and different from other types of motions. As container 630 is being tilted and shaken to dispense a pill, motion sensor data from motion sensor 660 can be sent to one of the previously discussed processors. The processor can analyze the motion sensor data to determine if it matches a distinctive motion of a medication being dispensed, and, accordingly, to determine whether the medication was dispensed.

In some embodiments, the processor can further analyze the motion sensor data to determine the amount or quantity of the dose of the medicine that was dispensed. For example, when container 630 is a container designed to release a single pill each time the container is tilted and shaken, the processor can analyze the motion sensor data to determine how many times container 630 was tilted and shaken to release a pill. As another example, when container 630 is a container containing eye drops, and one drop is released each time the container is compressed, the processor can analyze the motion sensor data to determine how many times the container was compressed. The technique disclosed in this specification can be applied to a wide variety of distinctive motions associated with dispensing a variety of types of medications, both to determine whether the medication was dispensed and the amount or quantity of the dose of the medication that was dispensed.

In some embodiments, medicine dispensing system 600 is able to send a message that identifies the medicine being dispensed. For example, PCB 650 can include a storage device, such as a read only memory (ROM) or flash memory, that stores an identity of the medication. A communication device or module of medicine dispensing system 600 can send the identity of the medication to another device or module.

FIGS. 8A and 8B are, respectively, views of a first and a second medication device that attach to a smart phone via, respectively, a first and a second mechanism, consistent with various embodiments. FIG. 8A illustrates smart phone 810, medication device 825, and container 830 all physically coupled with each other. Container 830 is inserted in medication device 825, which holds container 830. Medication device 825 is physically connected to smart phone 810 with the use of an attachment component, which, in the embodiment of FIG. 8A, is a micro-USB (Universal Serial Bus) connector. In various embodiments, an attachment component can be part of medication device 820, as shown in FIGS. 8A and 8B, or can be a separate component that can be physically connected to medication device 820 (not shown). Because all three objects 810, 825, and 830 are physically coupled with each other, they all move in unison.

FIG. 8B illustrates smart phone 810, medication device 820, and container 830 all physically coupled with each other. Container 830 is inserted in medication device 820, which holds container 830. Medication device 820 is physically connected to smart phone 810 with the use of an attachment component, which, in the embodiment of FIG. 8B, is attachment component 850. Because all three objects 810, 820, and 830 are physically coupled with each other, they all move in unison.

While two specific configurations of an attachment component have been described, it is understood that the disclosed technology can be applied to a wide variety of attachment components. As those of ordinary skill will understand, a suitable attachment component can take any of various forms. In some embodiments, the attachment component is a connector. The connector can be, for example, an Apple Lightning connector, an Apple 30-pin connector, an Apple Thunderbolt connector, as a full size USB connector, a standard USB connector, a standard A-type USB connector, a B-type USB connector, a mini USB connector, a mini USB A-type connector, a mini USB B-type connector, a micro-USB connector, a micro-USB A-type connector, a micro-USB B-type connector, a UC-E6 connector, etc. Further, the attachment component can be any physical component that can attach a medication device to a mobile device. In various embodiments, an attachment component can clamp on to smart phone 810, can adhere to smart phone 810, such as utilizing Velcro™ or an adhesive, can attach to smart phone 810, such as with the use of a fastener, etc.

In the embodiments of FIGS. 8A and 8B, medication devices 820 and 825 do not include a motion sensor. A processor, such as a processor of smart phone 810 or of a remote computer, can analyze data from a motion sensor of smart phone 810 to determine motion of the three objects that are physically coupled. In some embodiments, a medication device includes a connector, such as medication device 825 which includes micro-USB connector 855, which is inserted in a compatible connector of a mobile device, such as smart phone 810, to enable the two devices to communicate. In some embodiments, a medication device communicates wirelessly with the mobile device. In some embodiments, a medication device, such as medication device 820, does not contain or include any electronics.

A user can attach medication device 820 or 825 to smart phone 810 in preparation for dispensing medicine, such as pill 840, from container 830. In the embodiments of FIGS. 8A and 8B, smart phone 810 includes a medication monitoring application. As the user prepares to dispense medicine from container 830, the medication monitoring application, which is running in the background, determines that medicine may be about to be dispensed. In some embodiments, medication device 820 or 825 can include a sensor that triggers when the user takes some action that can be sensed by the sensor.

For example, medication device 820 or 825 can include a tactile sensor that the user triggers when he touches the device in preparation to dispense medicine. Medication device 820 or 825, based on data from the tactile sensor that indicates that the user touched the device, can send a signal to smart phone 810. The medication monitoring application, based on the signal, can begin to analyze motion sensor data from a motion sensor of smart phone 810. Based on motion sensor data that indicates a distinctive motion of medicine being dispensed from a container, smart phone 810 can determine that medication was dispensed from container 830. In some embodiments, data from a sensor of medication device 820 or 825 is analyzed by a processor to determine that medication was dispensed from container 830.

In embodiments where a medication device, such as medication device 820, does not include any electronics, a medication monitoring application can continuously analyze motion sensor data of the motion sensor of smart phone 810 to determine when medicine is dispensed. Using techniques similar to those discussed above, the medication monitoring application can analyze the motion sensor data to determine if it matches a distinctive motion of a medication being dispensed, and, accordingly, to determine whether the medication was dispensed. In some embodiments, using techniques similar to those discussed above, the medication monitoring application can further analyze the motion sensor data to determine the amount or quantity of the dose of the medicine that is dispensed.

However, continuously monitoring sensor data may consume more power than is desirable, or than is needed. To reduce power, the sensor data can be analyzed when data is received that indicates that medicine is about to be dispensed. The medication monitoring application can detect that medicine is about to be dispensed in several ways. For example, the user can use the user interface of smart phone 810 to launch the medication monitoring application, indicating that medicine is about the be dispensed, or to otherwise signal to the medication monitoring application that the medicine is about to be dispensed. Based on being launched or otherwise notified, the medication monitoring application can begin to analyze motion sensor data from the motion sensor of smart phone 810 to determine if medication is being dispensed.

In some embodiments, using techniques similar to those discussed above, the medication monitoring application analyzes data from other sensors of medication device 820 or 825, such as an optical sensor or a pressure sensor, to determine if any medicine was dispensed, and/or the amount or quantity of the dose of the medicine that was dispensed.

Figure 9:
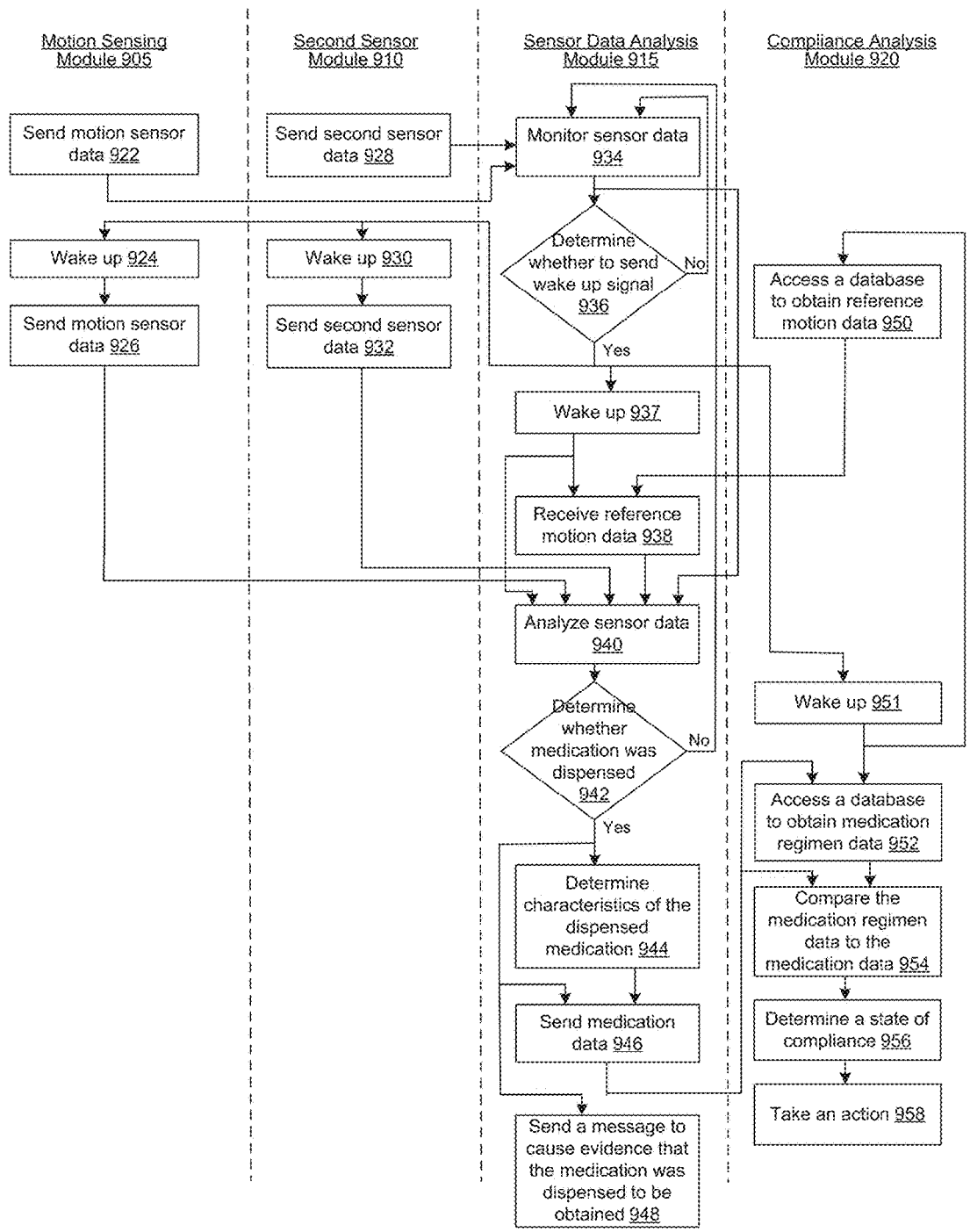
FIG. 9 is an activity diagram illustrating an example process of monitoring adherence to a medication regimen using a sensor, consistent with various embodiments.

FIG. 9 is an activity diagram illustrating an example process of monitoring adherence to a medication regimen using a sensor. The example process of FIG. 9 begins with sensor data analysis module 915, which in some embodiments can be in a low power mode, monitoring sensor data (step 934). Sensor data analysis module 915 is a module that analyzes motion sensor data in association with monitoring adherence to a medication regimen.

Sensor data analysis module 915 monitors motion sensor data from motion sensing module 905. Motion sensing module 905 is a module that includes a motion sensor that can move in unison with a medicine container. For example, medication device 410 of FIG. 4, which moves in unison with container 420 when physically coupled to container 420 as illustrated in FIG. 4, can include motion sensing module 905. As a second example, smart phone 810, which moves in unison with container 830 when physically coupled to container 830 as illustrated in FIGS. 8A and 8B, can include motion sensing module 905. When the motion sensor of motion sensing module 905 generates motion sensor data, motion sensing module 905 sends the motion sensor data to sensor data analysis module 915 (step 922).

In some embodiments, sensor data analysis module 915 also monitors sensor data from a second sensor (step 934). As discussed above in the description of FIG. 6, the second sensor can be used to detect if medicine has been released from a medicine container, and/or can be used to determine the amount or quantity of the dose of medicine that was released. The second sensor can be, for example, a pressure sensor, an optical sensor, a sound sensor, an electrical current sensor, a fluid sensor, a fluid velocity sensor, a force sensor, a chemical sensor, a magnetic field sensor, an electrical field sensor, a drop sensor, a heat sensor, a tactile sensor, etc.

Second sensor module 910 is a module that includes the second sensor. In some embodiments, the motion sensor of motion sensing module 905 can be used to detect if medicine has been released from the container and/or to determine the amount or quantity of the dose of medicine released. The second sensor and second sensor module 910 may be omitted from these embodiments, as the second sensor is not needed to detect if medicine has been released from the container and/or to determine the amount or quantity of the dose of medicine released. In some embodiments, second sensor module 910 sends data from the second sensor to sensor data analysis module 915 (step 928).

After receiving the sensor data of step 934, sensor data analysis module 915 can determine whether to send a wake up signal (step 936). In various embodiments, the wake up signal can be sent to any of motion sensing module 905, second sensor module 910, sensor data analysis module 915, or compliance analysis module 920, any or all of which can be in a low power state. Sensor data analysis module 915 can analyze the motion sensor data to determine if the data indicates that medicine may be about to be dispensed and to determine whether to send a wake up signal (step 936).

When sensor data analysis module 915 determines that medicine may be about to be dispensed, the module can send a wake up signal. When sensor data analysis module 915 determines that medicine is not about to be dispensed, the module can continue monitoring sensor data (step 934).

For example, motion sensor data received from motion sensing module 905 can indicate that the motion sensor, and/or a medicine container to which the motion sensor is physically coupled, moved farther than a pre-determined amount, such as three inches. Based on the motion sensor data and/or the associated indication of movement, sensor data analysis module 915 can determine that medicine may be about to be dispensed, and can determine to send a wake up signal. As another example, the second sensor can be a tactile sensor and tactile sensor data received from second sensor module 910 by sensor data analysis module 915 can indicate that a person touched the tactile sensor and/or touched a container that can be used to dispense medicine. Based on the second sensor data, sensor data analysis module 915 can determine that medicine may be about to be dispensed, and can determine to send a wake up signal. As yet another example, motion sensor data received from motion sensing module 905 can indicate that the bottle moved less than a pre-determined amount, such as three inches. Based on the motion sensor data and/or the associated indication of movement, sensor data analysis module 915 can determine that medicine is not about to be dispensed, and can continue monitoring sensor data (step 934).

Steps 924, 930, 937, and 951 are steps that can occur in embodiments where, respectively, motion sending module 905, second sensor module 910, sensor data analysis module 915, and compliance analysis module 920 enter a low power state. At steps 924, 930, 937, and 951, motion sending module 905, second sensor module 910, sensor data analysis module 915, and compliance analysis module 920, respectively, wake up. When a module "wakes up," the module awakens from a low power reduced functionality/activity state and enters a normal state where the module can perform normal functions/activities. For example, after waking up at steps 924, 930, 937, and 951, motion sending module 905, second sensor module 910, sensor data analysis module 915, and compliance analysis module 920 can, respectively, send motion sensor data (step 926), send second sensor data (step 932), receive reference motion data (step 938) and/or analyze sensor data (step 940), and/or access a database to obtain reference motion data (step 950) and/or to obtain medication regimen data (step 952).

In the example process of FIG. 9, a user grabs a medicine container and is going to dispense medicine. As the user moves the container, motion sensing module 905 and its motion sensor, being physically coupled to the container, move in unison with the container. Motion sensing module 905 sends motion sensor data generated by the motion sensor to sensor data analysis module 915 (step 926). In some embodiments, as the user tilts the container and dispenses the medicine, the second sensor generates second sensor data which second sensor module 910 sends to sensor data analysis module 915 (step 932).

Sensor data analysis module 915 analyzes any of the motion sensor data and/or the second sensor data (step 940) to determine whether medication was dispensed (step 942). In some embodiments, sensor data analysis module 915 analyzes the second sensor data (step 940) to determine whether medication was dispensed (step 942), and/or to determine characteristics of the medication that was dispensed (step 944), such as the amount or quantity of the dispensed dose, the date/time that the dose was dispensed, etc. For example, medicine dispensing system 600 of FIG. 6 includes optical sensor 620, which is a second sensor, and, in some embodiments, the optical sensor data is analyzed to determine whether medicine was dispensed, and/or the amount or quantity of the dose of medicine that was dispensed.

In some embodiments, sensor data analysis module 915 analyzes the motion sensor data (step 940) to determine whether medication was dispensed (step 942), and/or to determine the characteristics of the medicine that was dispensed (step 944). For example, medicine dispensing system 600 includes motion sensor 660, and, in some embodiments, the motion sensor data is analyzed to determine whether medicine was dispensed, and/or the amount or quantity of the dose of medicine that was dispensed.

Sensor data analysis module 915 can analyze the motion sensor data in any of various ways, including those discussed above. For example, in some embodiments, sensor data analysis module 915 receives reference motion data from compliance analysis module 920 (step 938), which compliance analysis module 920 can have obtained from a database (step 950). The reference motion data can include data indicating motions characteristic of users who are about to dispense or are dispensing a medication. Sensor data analysis module 915 can compare the reference motion data to the sensor data from motion sensing module 905, and, based on the comparison, can determine whether medication was dispensed (step 942), and/or the amount or quantity of the dose of medication dispensed (step 944).

Pharmaceutical companies run drug studies as part of drug development programs. One of the issues that pharmaceutical companies experience during drug studies is non-adherence of the study participants to the medication regimen of the drug study. To increase the accuracy of the results from these drug studies, many pharmaceutical companies want to increase the accuracy of monitoring study participant adherence to the medication regiment. To further this goal, some pharmaceutical companies would like to obtain evidence above and beyond the sensor data to be able to more accurately verify that a drug study participant adhered to the medication regimen.

In some embodiments, sensor data analysis module 915 sends a message to cause additional evidence that the medication was dispensed to be obtained (step 948). For example, sensor data analysis module 915 can send a message to a medication monitoring application running on a mobile device. The medication monitoring application, based on the message, can: prompt the user to identify the medication; cause the mobile device to, or prompt the user to, take a photo, record a video, or activate an audio recorder; etc. This photo/video/audio data can be manually analyzed by pharmaceutical company employee, or can be automatically analyzed by a computer system, to further validate compliance to the medication regimen.

For example, when a video shows the user applying the medicine, such as when the medicine is an eye drop and the medication device of the embodiment of FIG. 8A or 8B is being used to dispense the eye drop, the video can be analyzed to verify that the user actually applied the medication. As another example, video recorded by smart phone 810, e.g. based on receipt of the message of step 948, may show the smart phone being raised above the head of the user, and being held there for a period of time as the user administers the drops. In such a case, the video, while not actually showing the eye drops going into the eye of the user, can be analyzed to verify that it is consistent with the user applying the eye drops, providing additional evidence that the eye drops were administered.

As yet another example, when the photo or video shows a medicine label of the medicine container or the medicine itself, the photo/video can be analyzed to determine the identity of the medication being dispensed. As another example, the user can be prompted by the medication monitoring application to speak the name of the medication, and the audio recording can be analyzed to determine the identity of the medication being dispensed. As one more example, the medication monitoring application can display a graphical representation of the medicine(s) that the user is taking to prompt the user to touch the appropriate graphical representation to identify the medication being dispensed.

Sensor data analysis module 915 sends medication data to compliance analysis module 920 (step 946). The medication data can include the determination of whether the medication was dispensed, the date and/or time that the medication was dispensed, the amount or quantity of the medication that was dispensed, evidence that the medication was dispensed, etc. Compliance analysis module 920 is a module that analyzes the medication data to determine a state of compliance of a user to a medication regimen. Compliance analysis module 920 can access a database or other storage medium, such as a file, spreadsheet, etc., to obtain medication regimen data (step 952), which is data regarding a medication regimen.

Compliance analysis module 920 can compare the medication regimen data to the medication data (step 954) to determine a state of compliance to the medication regimen (step 956). In some embodiments, the medication regimen data includes times and dates that doses of a medication are to be taken and the associated amount or quantity of the medication. When compliance analysis module 920 receives medication data for a dose of medicine, it can compare the medication data to the medication regimen data to determine if the dose was taken at the right time, if the correct amount or quantity of medicine was taken, etc. The medication data can include the time and/or date that a medication was dispensed, and the amount or quantity of the dose of the medication. In some embodiments, the medication regimen data and the medication data both include an identity of the medication. Compliance analysis module 920 can compare these two medication identities to determine whether the user is adhering to or complying with the medication regimen.

When compliance analysis module 920 compares the medication regimen data to the medication date, the comparison can include tolerance margins. For example, a dose of a medication can comply with a medication regimen if the time that the medication was dispensed/administered is within a predetermined tolerance margin of the time indicated by the medication regimen for the dose. As another example, a dose of medication can comply if the amount or quantity of the medication dispensed/administered is within a predetermined tolerance margin of the dose as indicated by the medication regimen.

The tolerance margin can further be based on a function that takes into account medication data of other doses. In some embodiments, the tolerance margin for a particular dose of medicine is based on previous doses of the medicine. For example, where previous doses were administered very close to the regimen time, the function may allow the tolerance margin the for the current dose to increase as compared to the tolerance margin for an earlier dose.

Based on the determined state of compliance, the medication data, and/or the medication regimen data, compliance analysis module 920 can take an action (step 958). The action taken can be any of various actions, such as sending a message that indicates the state of compliance, sending a message to cause the user to be notified to take, not take, delay taking, etc., a medication, sending a message to cause a prescription to be renewed and/or refilled, etc. A message that indicates the state of compliance can be sent to any of various parties, such as to the user (via a device such as a mobile device or computer system), to a medical professional associated with the user, to a relative of the user, to a pharmacy, to an insurance company, to a member of a drug study of which the user is a participant, etc.

In some embodiments, the message can notify the various parties that the user is not adhering to the medication regimen, and can provide details as to the type of issue. For example, the message can notify the various parties that the user missed one dose of the medication, or has missed all doses for the past week. As another example, the message can notify the various parties that the user, while taking all the doses, is not taking the doses close enough to the time indicated by the medication regimen.

FIGS. 10A-G are block diagrams illustrating a variety of combinations of devices that can execute the example process of FIG. 9, consistent with various embodiments. Each of FIGS. 10A-G includes four modules from FIG. 9, motion sensing module 905, second sensor module 910, sensor data analysis module 915, and compliance analysis module 920. Each module can perform the activities represented in the column below the module in FIG. 9. Further, these modules are not all required to execute the example process of FIG. 9, and in some embodiments, a subset of these modules can be used to execute the process. While these figures represent a variety of combinations of devices that can execute the example process of FIG. 9, the combinations identified are not exhaustive and other combinations of devices are possible. For example, the process can be executed by a medication device that includes the four modules from FIG. 9, and such a medication device is not identified in any of FIGS. 10A-G.

Figure 10A:
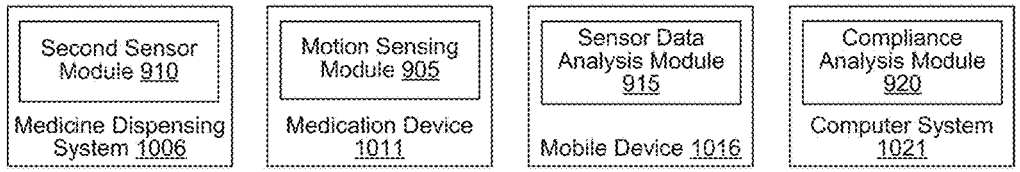
FIGS. 10A-G are block diagrams illustrating a variety of combinations of devices that can execute the example process of FIG. 9, consistent with various embodiments.

FIG. 10A includes four devices, medicine dispensing system 1006 which includes second sensor module 910, medication device 1011 which includes motion sensing module 905, mobile device 1016 which includes sensor data analysis module 915, and computer system 1021 which includes compliance analysis module 920. Medicine dispensing system 1006 can be, for example, medicine dispensing system 600 of FIG. 6. Medication device 1011 can be, for example, medication devices 100, 310, or 410 of FIGS. 1, 3 and 4. One difference between a medication dispensing system and a medication device is that a medication dispensing system includes an integrated medicine container, while a medicine device is configured such that it can be physically coupled to a physically separate medicine container, such as by holding the container or being attached to the container. Mobile device 1016 can be, for example, smart phone 810 of FIG. 8A or 8B. Computer system 1021 can be, for example, processing device 1100 of FIG. 11.

Figure 10B:
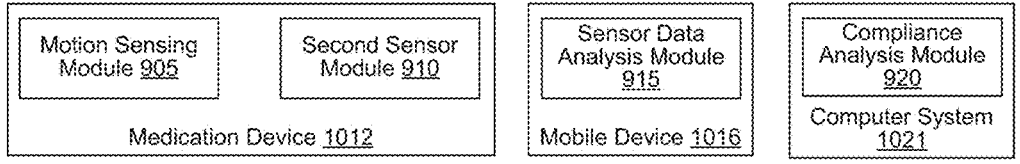

FIG. 10B includes three devices, medication device 1012 which includes motion sensing module 905 and second sensor module 910, mobile device 1016, and computer system 1021. Medication device 1012 can be, for example, medication device 100, 310, 410, 825, or 820 of, respectively, FIG. 1, 3, 4, 8A, or 8B in embodiments where the medication device includes both a motion sensor and a second sensor.

Figure 10C:
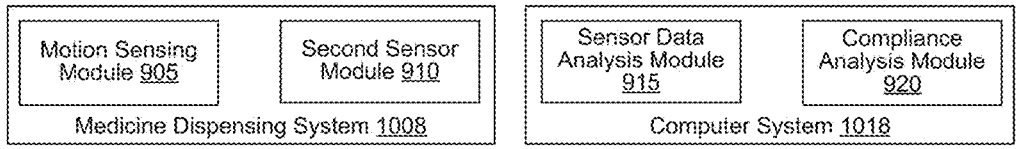

FIG. 10C includes two devices, medicine dispensing system 1008 which includes motion sensing module 905 and second sensor module 910, and computer system 1018, which includes sensor data analysis module 915 and compliance analysis module 920. Medicine dispensing system 1008 can be, for example, medicine dispensing system 600 of FIG. 6 in embodiments where medicine dispensing system 600 includes both a motion sensor and a second sensor. Computer system 1018 can be, for example, smart phone 810 of FIG. 8A or 8B.

Figure 10D:
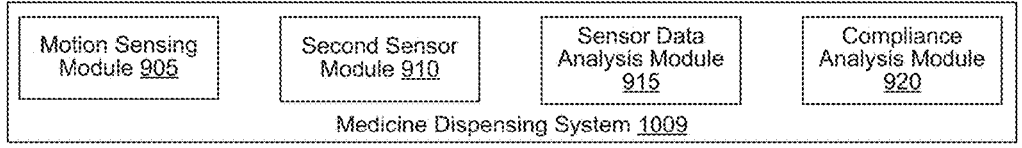

FIG. 10D includes one device, medicine dispensing system 1009, which includes motion sensing module 905, second sensor module 910, sensor data analysis module 915, and compliance analysis module 920. Medicine dispensing system 1009 can be, for example, medicine dispensing system 600 of FIG. 6 in embodiments where medicine dispensing system 600 includes both a motion sensor and a second sensor, and has the processor, storage, etc. needed to support the integration of sensor data analysis module 915 and compliance analysis module 920.

Figure 10E:
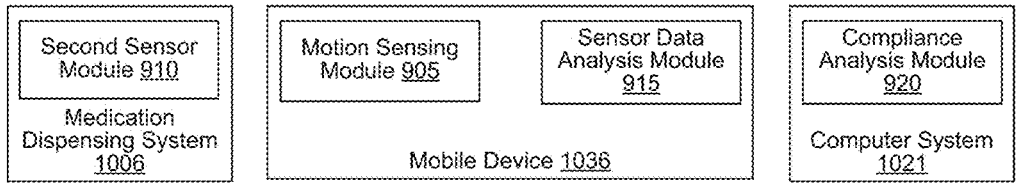

FIG. 10E includes three devices, medicine dispensing system 1006, mobile device 1036 which includes motion sensing module 905 and sensor data analysis module 915, and computer system 1021. Mobile device 1036 can be, for example, smart phone 810 of FIG. 8A or 8B.

Figure 10F:
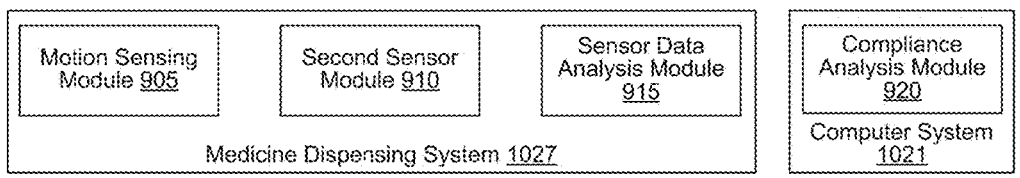

FIG. 10F includes two devices, medicine dispensing system 1027 which includes motion sensing module 905, second sensor module 910, and sensor data analysis module 915, and computer system 1021. Medicine dispensing system 1027 can be, for example, medicine dispensing system 600 of FIG. 6 in embodiments where medicine dispensing system 600 includes both a motion sensor and a second sensor, and has the processor, storage, communication, etc. needed to support the integration of sensor data analysis module 915.

Figure 10G:
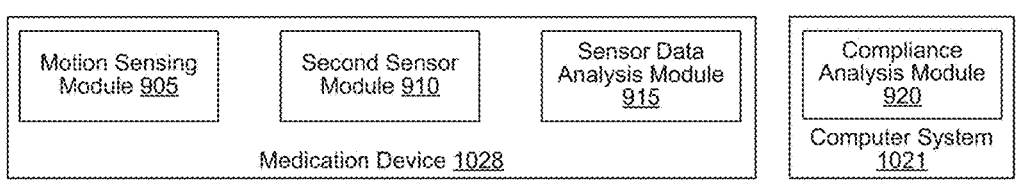

FIG. 10G includes two devices, medication device 1028 which includes motion sensing module 905, second sensor module 910, and sensor data analysis module 915, and computer system 1021. Medication device 1028 can be, for example, medication device 100, 310, or 410, of FIG. 1, 3, or 4 in embodiments where medication device 100, 310, or 410 include both a motion sensor and a second sensor, and have the processor, storage, communication, etc. needed to support the integration of sensor data analysis module 915.

Figure 11:
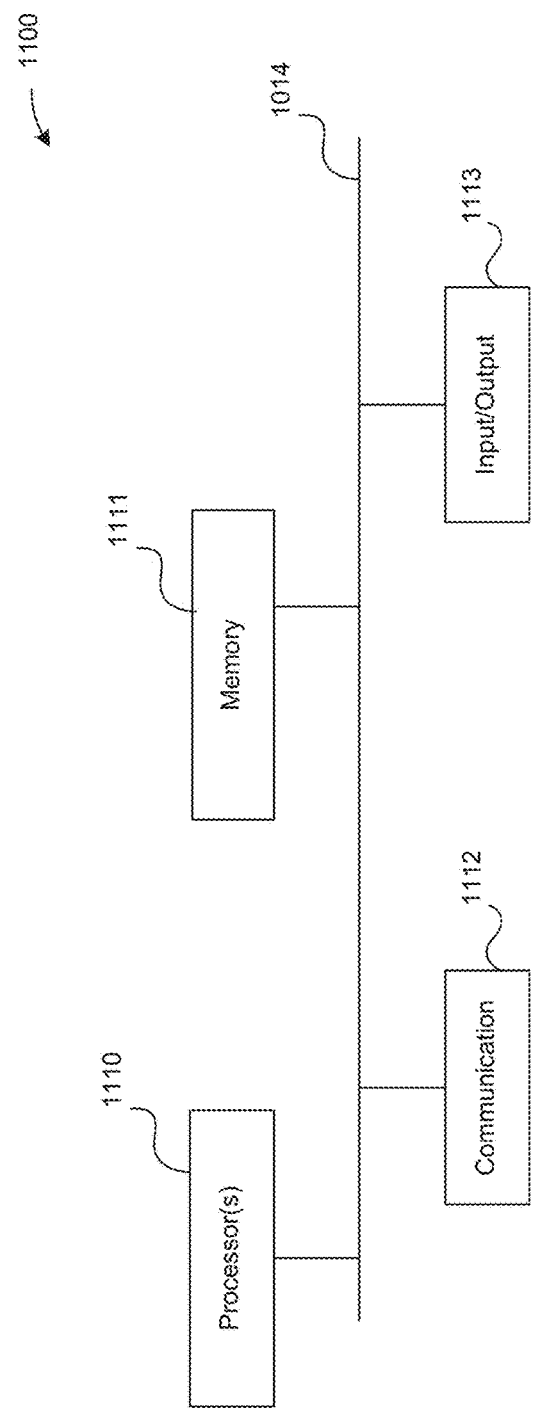
FIG. 11 is a block diagram illustrating an example of a processing system in which at least some operations described herein can be implemented, consistent with various embodiments.

FIG. 11 is a block diagram illustrating an example of a processing system in which at least some operations described herein can be implemented, consistent with various embodiments. Processing device 1100 can represent any of the devices described above, e.g., the medication device, the medicine dispensing system, the mobile device, or the computer system. Any of these systems can include two or more processing devices, as is represented in FIG. 11, which can be coupled to each other via a network or multiple networks.

In the illustrated embodiment, the processing system 1100 includes one or more processors 1110, memory 1111, a communication device 1112, and one or more input/output (I/O) devices 1113, all coupled to each other through an interconnect 1114. The interconnect 1114 may be or include one or more conductive traces, buses, point-to-point connections, controllers, adapters and/or other conventional connection devices. The processor(s) 1110 may be or include, for example, one or more general-purpose programmable microprocessors, microcontrollers, application specific integrated circuits (ASICs), programmable gate arrays, or the like, or any combination of such devices. The processor(s) 1110 control the overall operation of the processing device 1100. Memory 1111 may be or include one or more physical storage devices, which may be in the form of random access memory (RAM), read-only memory (ROM) (which may be erasable and programmable), flash memory, miniature hard disk drive, or other suitable type of storage device, or any combination of such devices. Memory 1111 may store data and instructions that configure the processor(s) 1110 to execute operations in accordance with the techniques described above. The communication device 1112 may be or include, for example, an Ethernet adapter, cable modem, Wi-Fi adapter, cellular transceiver, Bluetooth transceiver, or the like, or any combination thereof. Depending on the specific nature and purpose of the processing device 1100, the I/O devices 1113 can include various devices, e.g., a display (which may be a touch screen display), audio speaker, keyboard, mouse or other pointing device, microphone, camera, sensor, etc.

Figure 12A:
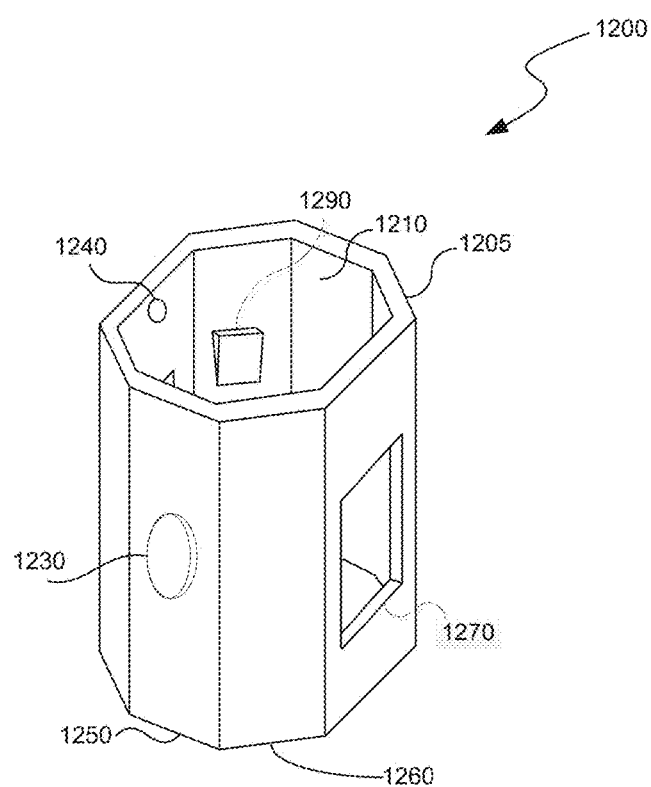
FIGS. 12A and 12B are illustrations of an example of a medication device, consistent with various embodiments.
Figure 12B:
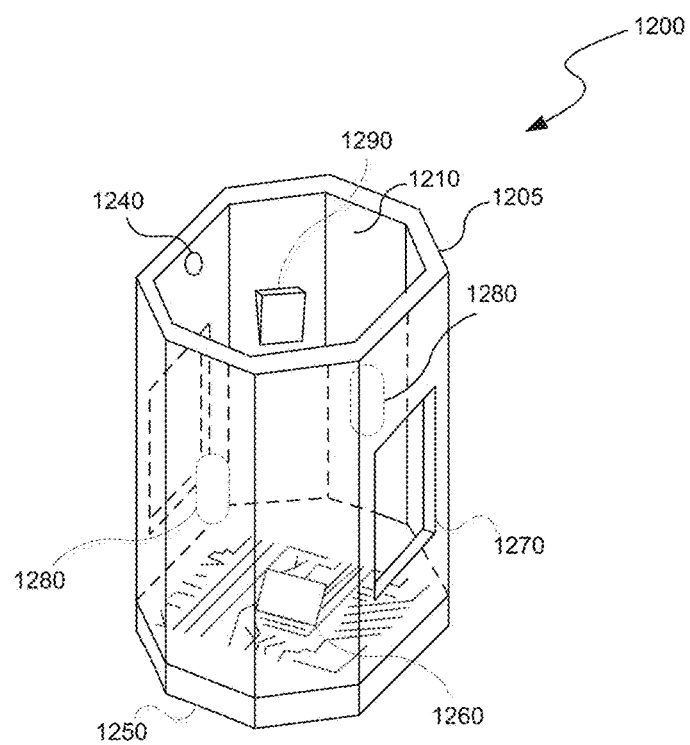

FIGS. 12A and 12B illustrate an example of a medication device, consistent with various embodiments. Medication device 1200 provides a jacket 1205 to enclose a container containing material or liquid within opening 1210, such as a bottle containing eye drops or pills, or an inhaler containing a gas, liquid, or powder. Jacket 1205 can include a tactile sensor 1230, a material/drop sensor 1240, an electronic module compartment 1250, one or more jacket apertures 1270, or some combination thereof. In some embodiments, a mechanical mechanism (e.g., wing pressure mechanism, lever, gripping member) for securing a container within opening 1210 of jacket 1205 is used. In other embodiments, the jacket 1205 is lined with a material that is flexible enough to allow for insertion of containers of varying sizes and shapes.

The medication device 1200 can comprise one or more jacket apertures 1270 that allow a user to apply pressure directly to the container positioned within opening 1210 of jacket 1205. When the user applies pressure to the container, matter is released from the container. In some embodiments, a material/drop detector sensor 1240 can detect when matter, such as a pill or a drop of liquid, leaves a container. Material/drop sensor 1240 could be an optical (e.g., LED/phototransistor) sensor capable of detecting if some matter has been released from the container. In these embodiments, when the matter is released from the bottle, the drop will block or refract a beam and cause the output of the optical sensor to fluctuate. Material/drop sensor 1240 can be placed at the top of the expansion pack and could be activated only when the container is in a specific position, as detected by a motion detector, to conserve power.

In other embodiments, one or more pressure sensors 1280 may be coupled to the jacket 1205 and positioned within the opening 1210. The pressure sensors 1280 are configured such that, when the user applies pressure to the container through the aperture 1270, the expansion of the container applies pressure to the one or more pressure sensors 1280. Although a specific jacket configuration and sensor type are discussed here and illustrated in FIGS. 12A and 12B, it is understood that a wide variety of jacket configurations and sensor types and placements can be used to detect when matter is dispensed or released from the container.

The one or more pressure sensors 1280 can be configured to communicate information (e.g., time medication was dispensed, quantity dispensed) to various modules housed within electronic module compartment 1250. For example, the pressure sensors 1280 can communicate information to a wireless communication module, which can be used to send and receive data to and from a computer or another portable communication device.

In some embodiments, a sensor 1290 is configured to sense whether the container has been placed within the opening 1210 of the jacket 1205. The sensor 1290 may be, for example, one of the one or more pressure sensors 1280. However, the sensor can be distinct from the one or more pressure sensors 1280. In various embodiments, the sensor 1290 can also be configured to provide a mechanism for securing the container within the opening 1210 of the jacket. For example, a wing pressure mechanism (e.g., wing pressure mechanism 120 of FIG. 1) may be arranged to secure the container.

Figure 17A:
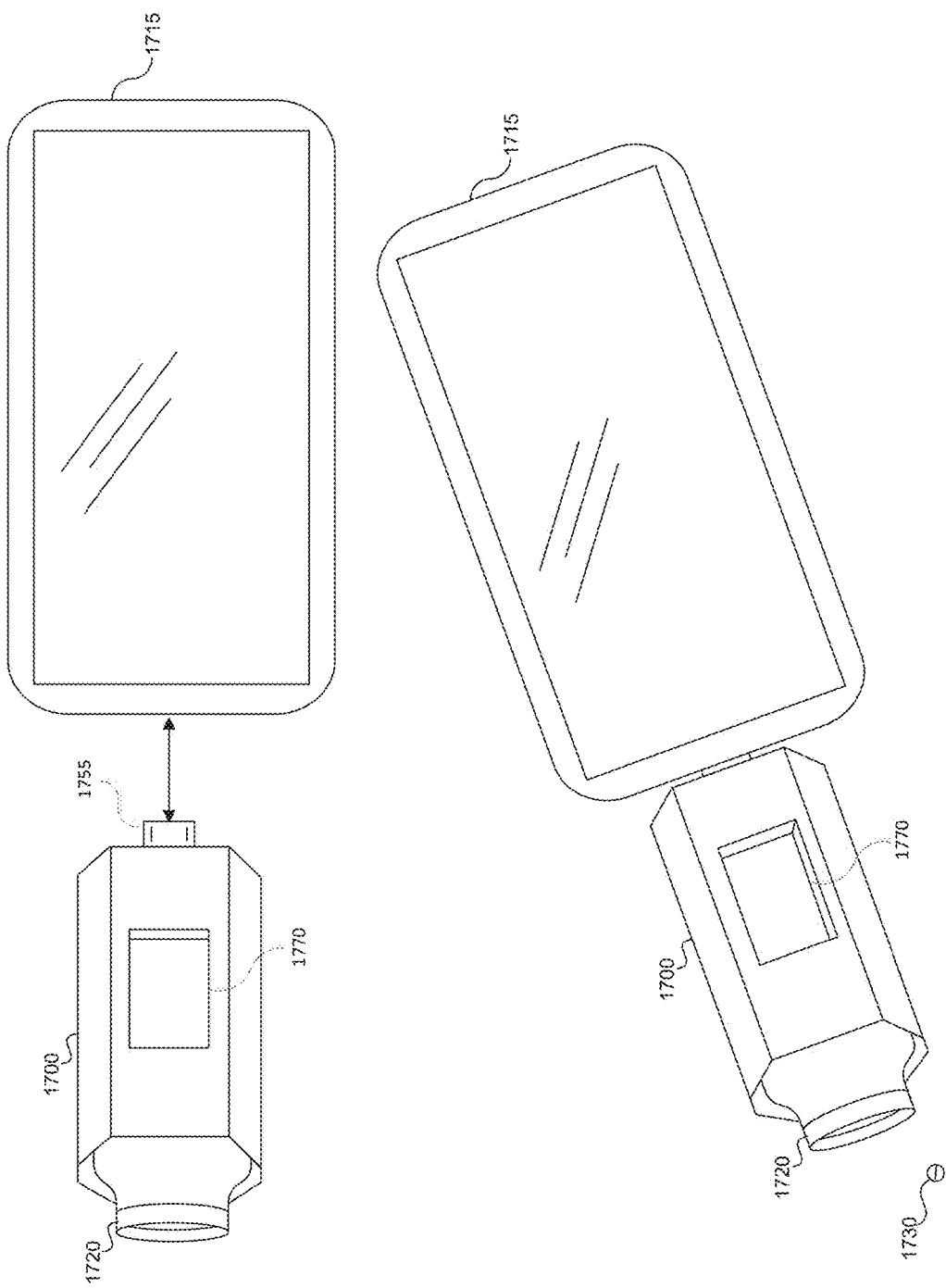
FIGS. 17A and 17B are, respectively, views of a first and a second medication device that attach to a smart phone via, respectively, a first and a second mechanism, consistent with various embodiments.
Figure 17B:
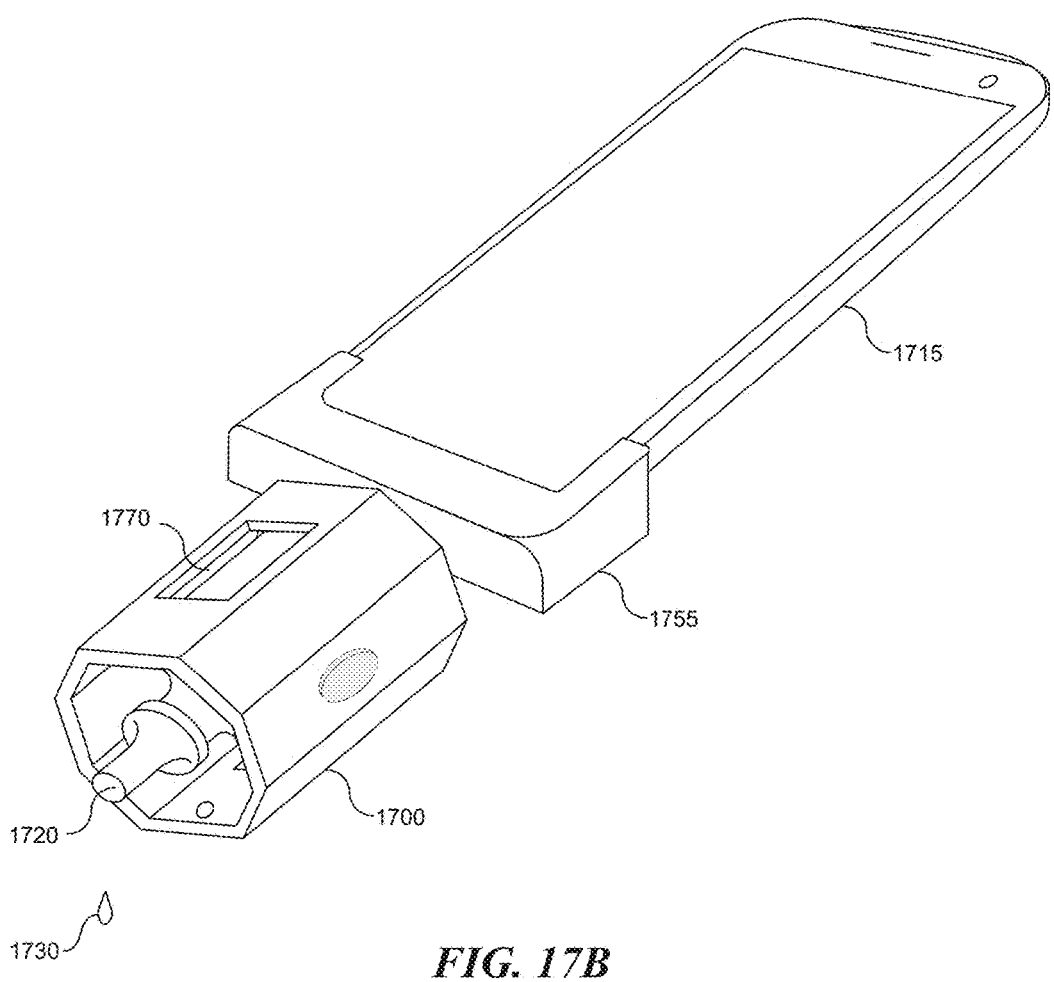

In some embodiments, the electronic module compartment 1250 houses a motion sensor 1260, and can house additional modules and/or components (e.g., processors, communication devices, integrated electronics, memory storage devices, batteries, sensors, etc.) of the medication device. Because the motion sensor 1260 is attached to or embedded in medication device 1200 and, resultantly, moves in unison with medication device 1200, the generated signals also indicate the motion of medication device 1200, and of any container that is held by or otherwise physically connected to medication device 1200. In some embodiments, the motion of medication device 1200 can be indicated by a motion sensor of a mobile device to which medication device 1200 is physically connected, as will be discussed in more detail below. The one or more pressure sensors 1280, which are physically connected to the medication device 1200, may be configured to remain off until the motion sensor 1260 senses movement of the medication device 1200. The one or more pressure sensors 1280 may also be configured to remain off until the sensor 1290 determines a container is within the opening 1210 of the jacket 1205 or user interacts with the tactile sensor 1230. FIGS. 17A and 17B illustrate medication devices 1700 that are similar to medication device 1200, physically connected to smart phone 1715, a mobile device, via different mechanisms.

Figure 13:
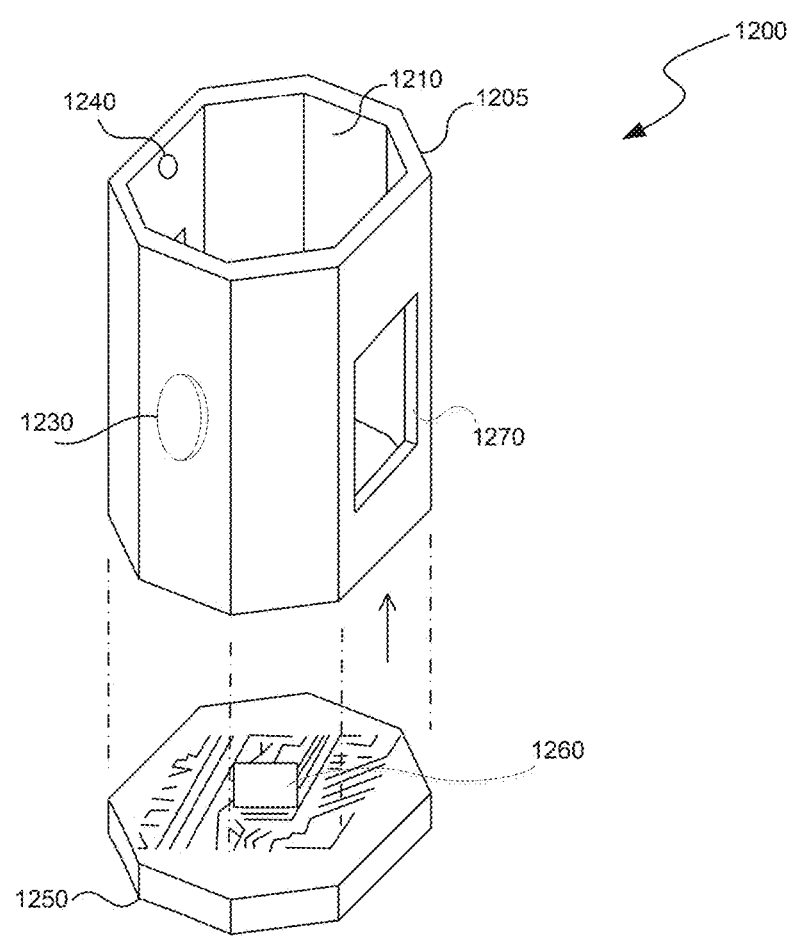
FIG. 13 is an expanded view of a medication device, consistent with various embodiments.

In some embodiments, jacket 1205 may have integrated electronics and components embedded throughout. For example, pressure sensors 1280 can be coupled to the jacket 1205 and positioned within opening 1210 or integrated into the physical structure of jacket 1205. As illustrated in FIG. 13, electronic module compartment 1250 can be removable from jacket 1205. As a result, some embodiments provide for a plurality of jackets, each having openings of different sizes and lengths to hold different sized or shaped medicine containers. The jackets can be removed and interchanged with the electronic module compartment 1250. The jackets can include mechanical, electrical, or electromechanical sensors (e.g., sensor 1290) for detecting whether a container is present within the opening 1210 of the jacket 1205. For example, in some embodiments, optical components or switches may be used to detect that a container is present within the jacket 1205. In other embodiments, a wing pressure mechanism can be used to detect whether a container is present within the opening 1210 of jacket 1205.

The medication device 1200 can also include an audio input device (e.g., microphone) or audio output device (e.g., speaker) to capture or project sound, respectively. For example, the jacket 1205 may include a microphone configured to record the patient dictating whether medication was taken, complications or side effects, etc. In some embodiments, the jacket 1205, and/or electronic module compartment 1250 include software or hardware configured for voice recognition. For example, a voice recognition module can be used to identify a patient, record patient feedback or side effects, report the feedback and/or side effects to a third party (e.g., physician, caretaker), etc. Various embodiments also include a speaker through which the medication device 1200 can project messages to the patient. The messages can be prerecorded and stored locally on the medication device 1200 or transmitted from a remote storage (e.g., via a wireless communication module). In some embodiments, the medication device 1200 is configured to play (i.e., project to the user) audio recordings in real-time that are recorded by a physician, caretaker, family member, etc.

In various embodiments, the medication device 1200 can determine whether medication was dispensed from the container based on data generated by the one or more pressure sensors 1280, the tactile sensor 1230, the material/drop sensor 1240, etc. The medication device 1200 can also determine whether medication was dispensed by analyzing data generated by more than one of the sensors described above. In some embodiments, one or more of these sensors may be configured to remain off or in sleep mode until motion sensor 1260 senses movement of the medication device 1200, the user interacts with the tactile sensor 1230, sensor 1290 determines the container is secured within the jacket 1205, etc.

Figure 14:
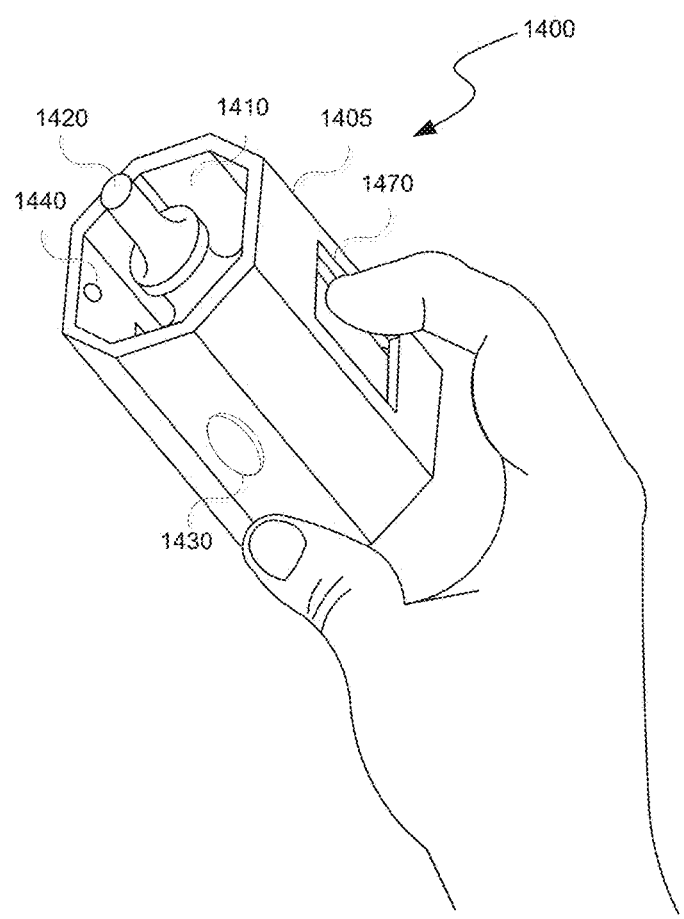
FIG. 14 is a side view of a user tilting a medication device, consistent with various embodiments.

FIG. 14 is a side view of a user tilting a portable medication device 1400, consistent with various embodiments. The medication device 1400 comprises a jacket 1405 that encloses a container 1420 containing material or liquid within opening 1410. The container can be, for example, a bottle containing eye drops as shown in FIG. 14. Jacket 1405 can include a tactile sensor 1430, a material/drop sensor 1440, an electronic module compartment, one or more jacket apertures 1470, one or more pressure sensors, or some combination thereof. The jacket apertures 1470 are configured to allow a user to apply pressure to the container 1420 positioned within the opening 1410 of jacket 1405. As the user applies pressure to the container 1420, the expansion of the container can apply pressure to the pressure sensors positioned within the opening 1410.

Some embodiments comprise a material/drop sensor 1440 and/or a tactile sensor 1430 that is capable of detecting if matter has been released from the container 1420. The tactile sensor 1430 can be configured to detect pressure applied by the user. The pressure detected by the tactile sensor 1430 is applied on the outside of the medication device 1400. In other embodiments, the medication device 1400 may comprise one or more pressure sensors (e.g., pressure sensors 1280) that are capable of detecting if matter has been released from the container 1420. The pressure detected by the one or more pressure sensors results from a user applying pressure to the container 1420 through an aperture 1470 of the jacket 1405.

Figure 15:
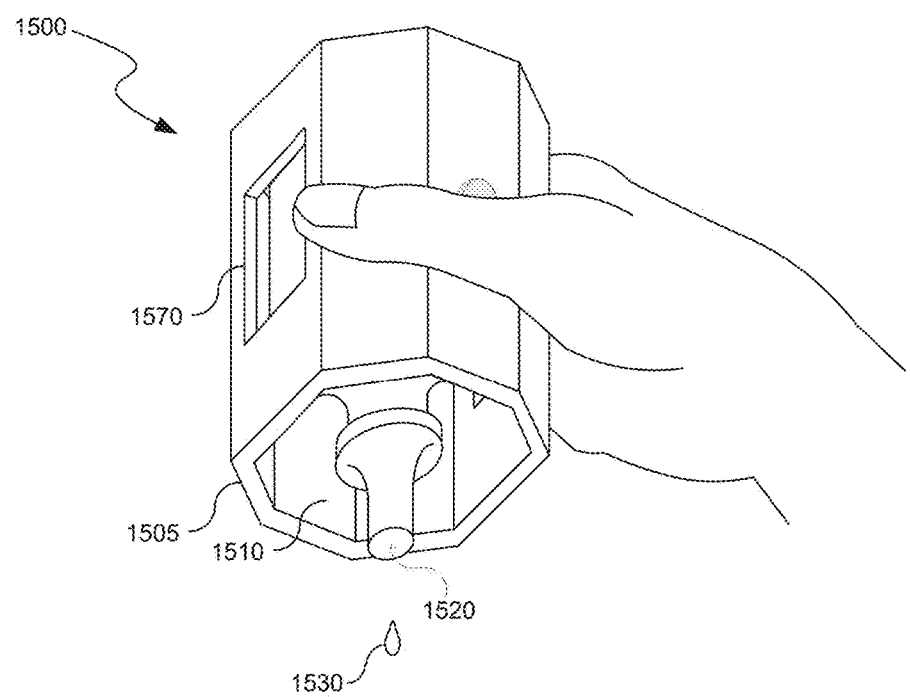
FIG. 15 is a view of a user using a medication device to distribute eye drops, consistent with various embodiments.
Figure 16:
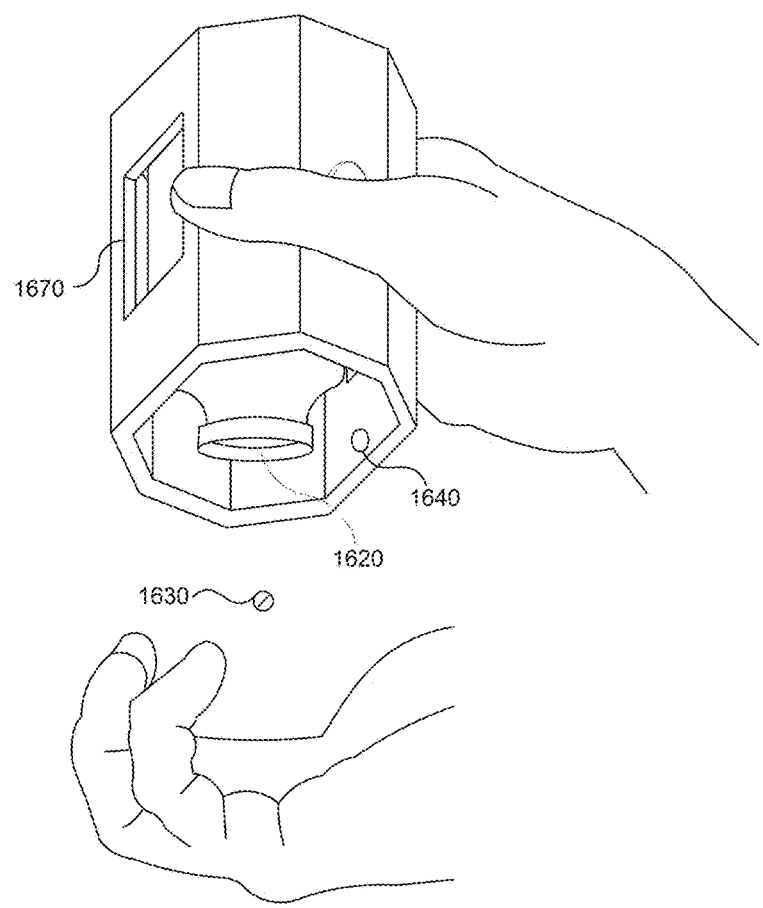
FIG. 16 is a view of a user using a medication device to distribute pills, consistent with various embodiments.

FIG. 15 is a side view of a user dispensing medication from a portable medication device 1500. Once a container 1520 is placed within the opening 1510 of the jacket 1505 and the user begins to interact with portable medication device 1500, various subsystems can be activated for tracking the user's activity. For example, when the user interacts (e.g., touches, moves) with the device, various sensors (e.g., drop sensors, motion sensors, pressure sensors) can be activated. Then, as the user tilts portable medication device 1500 upside down, as illustrated in FIG. 15, the sensors can determine whether matter, such as eye drop 1530, was released from container 1520. For example, if the user tilts portable medication device 1500 upside down, and applies pressure directly to the container 1520 through the one or more apertures 1570, a pressure sensor (e.g., pressure sensors 1280) may sense the expansion of the container 1520.

The lateral expansion sensed by the pressure sensor may indicate that a drop, pill, etc., has been dispensed from the container.

In some embodiments, a material/drop sensor 1640 can be used to determine if matter, such as a pill 1630, was released from container 1620 due to pressure applied to the container 1620 through the one or more jacket apertures 1670.

FIGS. 17A and 17B are, respectively, views of a first and a second medication device that attach to a smart phone via, respectively, a first and a second mechanism, consistent with various embodiments. FIG. 17A illustrates smart phone 1715, medication device 1700 having one or more jacket apertures 1770, and container 1720 all physically coupled to one another. Container 1720 is inserted into medication device 1700 and held within an opening. Medication device 1700 is physically connected to smart phone 1715 through the use of an attachment component, which, in the embodiment of FIG. 17A, is a micro-USB connector. In various embodiments, an attachment component can be part of the medication device 1700, as shown in FIGS. 17A and 17B, or can be a separate component that can be physically connected to medication device 1700 (not shown). Because all three objects 1700, 1715, and 1720 are physically coupled to one another, they all move in unison.

FIG. 17B illustrates smart phone 1715, medication device 1700, and container 1720 all physically coupled to one another. Container 1720 is inserted into medication device 1700 and held within an opening. Medication device 1700 is physically connected to smart phone 1715 with the use of an attachment component, which, in the embodiment of FIG. 17B, is attachment component 1755. Because all three objects 1700, 1715, and 1720 are physically coupled to one another, they all move in unison.

In various embodiments, the attachment component 1755 is configured to allow the user to apply pressure to the container 1720 through one or more jacket apertures 1770. The jacket apertures 1770 allow the user to apply a precise amount of force that ensures matter (e.g., eye drop 1730, pill) is dispensed from the container. When the user applies pressure to the container, the container expands. The expansion causes pressure to be applied to the one or more pressure sensors positioned within the opening of the jacket. When the pressure sensors detect expansion of the container, the medication device 1700 or a separate device (e.g., smart phone 1715, tablet, laptop) can track information related to various aspects of the user's medication regimen (e.g., time of treatment, quantity dispensed).

The disclosed technology can be utilized in various embodiments. For example, in some embodiments a medication device comprises: a jacket configured to hold a container of medicine, wherein the jacket includes an aperture that allows a user to apply pressure to the container to dispense medicine and a first pressure sensor arranged such that activation of the first pressure sensor indicates the container has been inserted into the jacket; a second pressure sensor coupled to the jacket and arranged such that activation of the second pressure sensor indicates the container has expanded in response to the user applying pressure to the container through the aperture; and a wireless communication module configured to exchange data recorded by the second pressure sensor with a communications device.

In some embodiments, the medication device further comprises a monitoring module configured to: activate the second pressure sensor in response to the first pressure sensor sensing the container has been inserted into the jacket; and deactivate the second pressure sensor in response to the first pressure sensor sensing the container has been removed from the jacket.

In some embodiments, the medication device further comprises one or more tactile sensors configured to activate and deactivate one or more motion sensors that detect movement of the jacket and the container. In some embodiments, the medication device further comprises a monitoring module configured to use the one or more motion sensors to monitor movement of the container and activate the second pressure sensor upon sensing movement. In some embodiments, the one or more tactile sensors measure pulse, heart rate, oxygen saturation, glucose concentration, or a combination thereof. In some embodiments, the medication device can acquire medical information (e.g., heart rate, glucose concentration) from another distinct device worn by the user.

In some embodiments, the medication device further comprises a medication detection sensor configured to sense medicine leaving the container and record data regarding medicine dispensed from the container. In some embodiments, the medication detection sensor includes an optical component to detect the medicine dispensed from the container. In some embodiments, the monitoring module is configured to activate the medication detection sensor upon sensing movement.

In some embodiments, the jacket further includes one or more light sources that convey visual information to the user, wherein the visual information conveyed to the user includes the user's progress towards completion of a medication regimen, quantity of medicine remaining in the container, a reminder to take medication, or a combination thereof. In some embodiments, the one or more light sources are light-emitting diodes. In some embodiments, the jacket includes one or more speakers that convey auditory information to the user.

In some embodiments, the first pressure sensor includes a wing pressure mechanism. In some embodiments, the jacket is one of a plurality of jackets having openings of different sizes to hold containers of various sizes. In some embodiments, the medication device includes a removable electronic compartment that can be attached with any of the plurality of jackets.

In some embodiments, the communications device is configured to convey visual and auditory information to the user, wherein the visual and auditory information includes the user's progress towards completion of a medication regimen, quantity of medicine remaining in the container, a reminder to take medication, or a combination thereof.

In some embodiments, a medication device comprises: a jacket configured to hold a container of medicine, wherein the jacket includes an aperture that allows a user to apply pressure to the container to dispense medicine and a first pressure sensor arranged such that activation of the first pressure sensor indicates the container has expanded in response to the user applying pressure to the container through the aperture; and an attachment component configured to enable the medication device to be physically connected to a mobile device, wherein the medication device causes a computer system to analyze a first data output generated by the first pressure sensor and received by the mobile device, and wherein the computer system determines whether medication was dispensed from the container based on the first data output.

In some embodiments, the computer system further analyzes a second data output from a motion sensor of the mobile device, wherein the second data output is indicative of motion of the medication device, the container, and the mobile device that move substantially in unison.

In some embodiments, the medication device further comprises: a second pressure sensor coupled to the jacket and arranged such that activation of the second pressure sensor indicates the container has been inserted into the jacket, wherein the second pressure sensor generates a third data output that indicates whether the container has been inserted into the jacket.

In some embodiments, the first pressure sensor is configured to be activated by the mobile device based on the second data output generated by the motion sensor of the mobile device or the third data output generated by the second pressure sensor.

In some embodiments, the medication device further comprises a medication detection sensor configured to indicate whether medication was dispensed from the container.

In some embodiments, the computer system is configured to: receive information from the medication device that includes time the medicine was dispensed, quantity of medicine dispensed, quantity of medicine remaining in the container, or a combination thereof; retrieve information from a storage device that includes information related to a medication regimen for the user; and determine a state of compliance to the medication regimen based on a comparison of the information received from the medication device and the information retrieved from the storage device.

In some embodiments, the information related to the medication regimen includes time information, which includes a planned time medicine is to be dispensed, and dosage information, which includes a planned type of medicine and a planned quantity of medicine to be dispensed. In some embodiments, the computer system is further configured to: send a message to the user or a physician that describes the user's state of compliance to the medication regimen. In some embodiments, a method for monitoring adherence to a medication regimen comprises: providing a medication device that includes a pressure sensor, wherein the medication device comprises a jacket that includes an interior cavity to secure a container of medicine and an aperture that allows a user to apply pressure to the container secured within the cavity, wherein the pressure sensor is configured to sense lateral expansion of the container in response to the user applying pressure to the container through the aperture, and wherein the pressure sensor generates data that indicates whether medicine has been dispensed from the container; recording the data in a storage; and communicating the data to a medical adherence system that is configured to track adherence to a medication regimen.

In some embodiments, the method further comprises: receiving a tactile input from the user through one or more interfaces located on the medication management device; and activating the pressure sensor upon receiving the tactile input. In some embodiments, the method further comprises: determining whether the container has been inserted into the interior cavity of the jacket.

In some embodiments, the method further comprises: providing, to the user, a reminder to dispense the medicine. In some embodiments, the reminder includes a visual or audible reminder.

Unless contrary to physical possibility, it is envisioned that (i) the methods/steps described above may be performed in any sequence and/or in any combination, and that (ii) the components of respective embodiments may be combined in any manner.

The techniques introduced above can be implemented by programmable circuitry programmed/configured by software and/or firmware, or entirely by special-purpose circuitry, or by any combination of such forms. Such special-purpose circuitry (if any) can be in the form of, for example, one or more application-specific integrated circuits (ASICs), programmable logic devices (PLDs), field-programmable gate arrays (FPGAs), etc.

Software or firmware to implement the techniques introduced here may be stored on a machine-readable storage medium and may be executed by one or more general-purpose or special-purpose programmable microprocessors. A "machine-readable medium", as the term is used herein, includes any mechanism that can store information in a form accessible by a machine (a machine may be, for example, a computer, network device, cellular phone, personal digital assistant (PDA), manufacturing tool, any device with one or more processors, etc.). For example, a machine-accessible medium includes recordable/non-recordable media (e.g., read-only memory (ROM); random access memory (RAM); magnetic disk storage media; optical storage media; flash memory devices; etc.), etc.

Note that any and all of the embodiments described above can be combined with each other, except to the extent that it may be stated otherwise above or to the extent that any such embodiments might be mutually exclusive in function and/or structure.

Although the present invention has been described with reference to specific exemplary embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense.

The invention claimed is:

1. A medication device comprising:
   a jacket configured to hold a container of medicine, wherein the jacket includes an aperture that allows a user to apply pressure to the container to dispense medicine and a first pressure sensor arranged such that activation of the first pressure sensor indicates the container has been inserted into the jacket;
   a second pressure sensor coupled to the jacket and arranged such that activation of the second pressure sensor indicates the container has expanded in response to the user applying pressure to the container through the aperture; and
   a wireless communication module configured to exchange data recorded by the second pressure sensor with a communications device.

2. The medication device of claim 1, further comprising a monitoring module configured to:
   activate the second pressure sensor in response to the first pressure sensor sensing the container has been inserted into the jacket; and
   deactivate the second pressure sensor in response to the first pressure sensor sensing the container has been removed from the jacket.

3. The medication device of claim 1, further comprising:
   an audio input device configured to record the user and transmit the recordings via the wireless communication module.

4. The medication device of claim 1, further comprising:
an audio output device configured to project a prerecorded audio recording or receive, and then project, an audio recording in real-time via the wireless communication module.

5. The medication device of claim 1, further comprising at least one of a temperature sensor, a humidity sensor, or a pressure sensor.

6. The medication device of claim 1, further comprising one or more tactile sensors configured to activate and deactivate one or more motion sensors that detect movement of the jacket and the container.

7. The medication device of claim 6, further comprising a monitoring module configured to use the one or more motion sensors to monitor movement of the container and activate the second pressure sensor upon sensing movement.

8. The medication device of claim 7, wherein the one or more tactile sensors measure pulse, heart rate, oxygen saturation, glucose concentration, or a combination thereof.

9. The medication device of claim 8, wherein a dose of medicine to be dispensed by the medication device is modified based on the user's pulse, heart rate, oxygen saturation, glucose concentration, or combination thereof measured by the one or more tactile sensors.

10. The medication device of claim 7, further comprising a medication detection sensor configured to sense medicine leaving the container and record data regarding medicine dispensed from the container.

11. The medication device of claim 10, wherein the medication detection sensor includes an optical component to detect the medicine dispensed from the container.

12. The medication device of claim 11, wherein the monitoring module is configured to activate the medication detection sensor upon sensing movement.

13. The medication device of claim 7, wherein the jacket further includes one or more light sources that convey visual information to the user, wherein the visual information conveyed to the user includes the user's progress towards completion of a medication regimen, quantity of medicine remaining in the container, a reminder to take medication, or a combination thereof.

14. The medication device of claim 13, wherein the one or more light sources are light-emitting diodes.

15. The medication device of claim 7, wherein the jacket includes one or more speakers that convey auditory information to the user.

16. The medication device of claim 7, wherein the first pressure sensor includes a wing pressure mechanism.

17. The medication device of claim 7, wherein the jacket is one of a plurality of jackets having openings of different sizes to hold containers of various sizes.

18. The medication device of claim 17, wherein the medication device includes a removable electronic compartment that can be attached with any of the plurality of jackets.

19. The medication device of claim 7, wherein the communications device is configured to convey visual and auditory information to the user, wherein the visual and auditory information includes the user's progress towards completion of a medication regimen, quantity of medicine remaining in the container, a reminder to take medication, or a combination thereof.

\* \* \* \* \*